(12) United States Patent
Adhikari et al.

(10) Patent No.: US 9,545,221 B2
(45) Date of Patent: Jan. 17, 2017

(54) ELECTRONIC SYSTEM WITH DYNAMIC LOCALIZATION MECHANISM AND METHOD OF OPERATION THEREOF

(71) Applicant: Samsung Electronics Co., Ltd., Suwon-si, Gyeonggi-Do (KR)

(72) Inventors: Suranjit Adhikari, San Jose, CA (US); Jeffrey Scott Pierce, Sunnyvale, CA (US); Stacie Lynn Hibino, San Jose, CA (US)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 242 days.

(21) Appl. No.: 14/518,921

(22) Filed: Nov. 25, 2014

(65) Prior Publication Data
US 2015/0145676 A1    May 28, 2015

Related U.S. Application Data

(60) Provisional application No. 61/909,521, filed on Nov. 27, 2013, provisional application No. 62/045,496, filed on Sep. 3, 2014.

(51) Int. Cl.
*G08B 1/08* (2006.01)
*A61B 5/11* (2006.01)
*A61B 5/00* (2006.01)

(52) U.S. Cl.
CPC ............ *A61B 5/1123* (2013.01); *A61B 5/1112* (2013.01); *A61B 5/681* (2013.01); *A61B 5/6824* (2013.01); *A61B 5/6828* (2013.01); *A61B 5/6831* (2013.01); *A61B 5/6898* (2013.01)

(58) Field of Classification Search
CPC ..... G08B 21/24; A61B 5/1123; A61B 5/1112; A61B 5/681; A61B 5/6824; A61B 5/6828; A61B 5/6831; A61B 5/6898

USPC ........ 340/539.32, 539.11–539.13, 571, 572.1
See application file for complete search history.

(56) References Cited

U.S. PATENT DOCUMENTS

| | | | |
|---|---|---|---|
| 7,602,301 B1 * | 10/2009 | Stirling | A61B 5/1127 340/573.1 |
| 7,668,613 B2 * | 2/2010 | Baier | G05B 19/41865 700/108 |
| 8,121,673 B2 * | 2/2012 | Tran | A61B 5/021 600/509 |
| 8,170,656 B2 | 5/2012 | Tan et al. | |

(Continued)

FOREIGN PATENT DOCUMENTS

| | | | | |
|---|---|---|---|---|
| WO | WO 2014124483 A1 * | 8/2014 | | G01S 5/0221 |
| WO | WO 2016033575 A1 * | 3/2016 | | G06F 1/16 |

OTHER PUBLICATIONS

Reinbolt et al., Determination of Patient-Specific Multi-Joint Kinematic Models Through Two-Level Optimization, Journal of Biomechanics Mar. 2005, 38(3): 621-626.

(Continued)

*Primary Examiner* — Eric M Blount
(74) *Attorney, Agent, or Firm* — IP Investment Law Group

(57) ABSTRACT

An electronic system includes a storage interface configured to access a kinematic model for representing one or more motions of a carrier; a control unit, coupled to the storage interface, configured to determine an attachment location of an attachable device based on the kinematic model; and generate a device setting based on the attachment location for provisioning the attachable device.

36 Claims, 10 Drawing Sheets

(56) References Cited

U.S. PATENT DOCUMENTS

| | | | | |
|---|---|---|---|---|
| 8,212,650 | B2* | 7/2012 | Tsern | G06F 1/1626 340/539.11 |
| 8,231,506 | B2* | 7/2012 | Molyneux | A43B 1/0054 340/572.1 |
| 8,369,936 | B2 | 2/2013 | Farringdon et al. | |
| 8,403,845 | B2 | 3/2013 | Stivoric et al. | |
| 8,461,998 | B2* | 6/2013 | Ruhs | A61B 5/11 340/573.1 |
| 8,994,827 | B2* | 3/2015 | Mistry | H04N 5/2252 348/158 |
| 9,037,530 | B2* | 5/2015 | Tan | A61B 5/0488 706/62 |
| 9,380,855 | B2* | 7/2016 | Anderson | A45F 5/00 |
| 2006/0202816 | A1 | 9/2006 | Crump et al. | |
| 2007/0279852 | A1* | 12/2007 | Daniel | A44C 5/0007 361/679.03 |
| 2008/0036737 | A1 | 2/2008 | Hernandez-Rebollar | |
| 2008/0058597 | A1 | 3/2008 | Arneson et al. | |
| 2008/0091373 | A1* | 4/2008 | McGibbon | A61B 5/1121 702/95 |
| 2008/0161707 | A1 | 7/2008 | Farringdon et al. | |
| 2008/0171915 | A1 | 7/2008 | Kawajiri et al. | |
| 2008/0294019 | A1 | 11/2008 | Tran | |
| 2009/0204031 | A1* | 8/2009 | McNames | A61B 5/1071 600/595 |
| 2009/0326833 | A1 | 12/2009 | Ryhanen et al. | |
| 2010/0176952 | A1 | 7/2010 | Bajcsy et al. | |
| 2013/0171596 | A1 | 7/2013 | French | |
| 2015/0057984 | A1* | 2/2015 | Nicoletti | G05B 15/02 703/2 |

OTHER PUBLICATIONS

Barry et al., Acoustic and Surface EMG Diagnosis of Pediatric Muscle Disease, Muscle Nerve, Apr. 1990, 13(4): 286-290.

* cited by examiner

ELECTRONIC SYSTEM WITH DYNAMIC LOCALIZATION MECHANISM AND METHOD OF OPERATION THEREOF

CROSS-REFERENCE TO RELATED APPLICATION(S)

This application claims the benefit of U.S. Provisional Patent Application Ser. No. 61/909,521 filed Nov. 27, 2013, the subject matter of which is hereby incorporated by reference herein, and U.S. Provisional Patent Application Ser. No. 62/045,496 filed Sep. 3, 2014, the subject matter of which is hereby incorporated by reference herein.

TECHNICAL FIELD

An embodiment of the present invention relates generally to an electronic system, and more particularly to a system with a dynamic localization mechanism.

BACKGROUND

Modern portable client and industrial electronics, especially client devices such as electronic watches, wristbands, portable health monitors, smartphones, tablets, and combination devices are providing increasing levels of functionality to support modem life including facilitating interactions with other portable devices and users of such devices. Research and development in the existing technologies can take a myriad of different directions.

As users become more empowered with the growth of portable devices, new and old paradigms begin to take advantage of this new device space. There are many technological solutions to take advantage of this new device capability to monitor the user and provide features according to the monitored result. However, such devices are often designed for operations surrounding one placement or attachment site on a body or object.

Thus, a need still remains for an electronic system with a dynamic localization mechanism appropriate for today's portable devices. In view of the ever-increasing commercial competitive pressures, along with growing client expectations and the diminishing opportunities for meaningful product differentiation in the marketplace, it is increasingly critical that answers be found to these problems. Additionally, the need to reduce costs, improve efficiencies and performance, and meet competitive pressures adds an even greater urgency to the critical necessity for finding answers to these problems. Solutions to these problems have been long sought but prior developments have not taught or suggested any solutions and, thus, solutions to these problems have long eluded those skilled in the art.

SUMMARY

An embodiment of the present invention provides an electronic system including: a storage interface configured to access a kinematic model for representing one or more motions of a carrier; a control unit, coupled to the storage interface, configured to: determine an attachment location of an attachable device based on the kinematic model; and generate a device setting based on the attachment location for provisioning the attachable device.

An embodiment of the present invention provides a method of operation of an electronic system including: determining an attachment location of an attachable device based on a kinematic model for representing one or more motions of a carrier; and generating a device setting based on the attachment location for provisioning the attachable device.

An embodiment of the present invention provides a non-transitory computer readable medium including instructions for execution by a control unit including: determining an attachment location of an attachable device based on a kinematic model for representing one or more motions of a carrier; and generating a device setting based on the attachment location for provisioning the attachable device.

Certain embodiments of the invention have other steps or elements in addition to or in place of those mentioned above. The steps or elements will become apparent to those skilled in the art from a reading of the following detailed description when taken with reference to the accompanying drawings.

DETAILED DESCRIPTION

Figure 1:
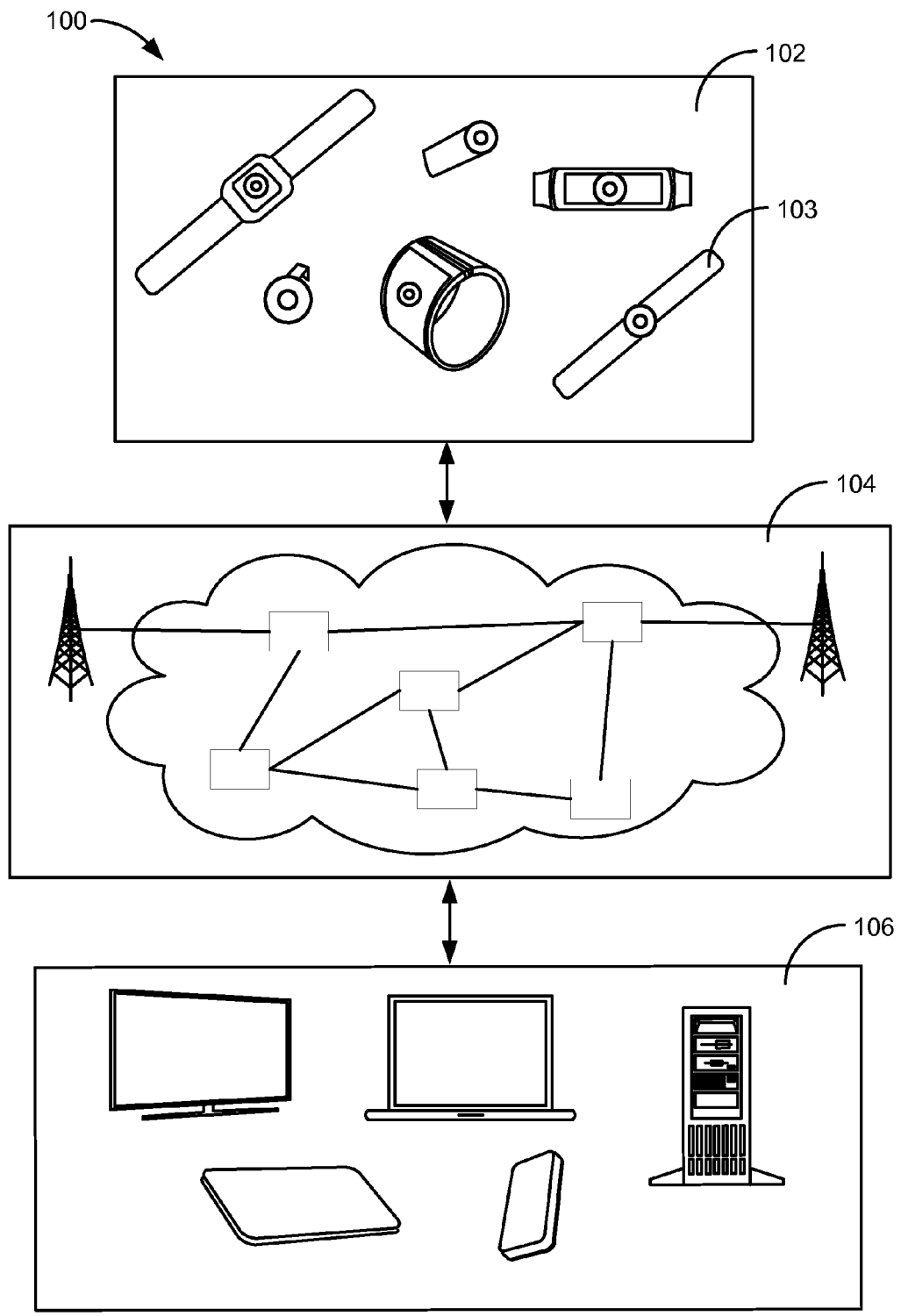
FIG. 1 is an electronic system with a dynamic localization mechanism in an embodiment of the present invention.

The following embodiments of the present invention provide an electronic system for automatically determining an attachment location of an attachable device based on a kinematic model of a carrier of the attachable device. The attachable device can also generate a device setting based on the attachment location for adapting the attachable device to the attachment location and utilizing a functionality of the attachable device suited for the attachment location.

An embodiment of the present invention can also generate an adjustable feedback at the attachable device based on the attachment location. The electronic system can generate the adjustable feedback based on the attachment location for enhancing a perceptibility of the adjustable feedback by the carrier.

The following embodiments are described in sufficient detail to enable those skilled in the art to make and use the invention. It is to be understood that other embodiments would be evident based on the present disclosure, and that system, process, or mechanical changes may be made without departing from the scope of the present invention.

In the following description, numerous specific details are given to provide a thorough understanding of the invention. However, it will be apparent that the invention may be practiced without these specific details. In order to avoid obscuring the embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation.

The term "module" referred to herein can include software, hardware, or a combination thereof in the embodiment of the present invention in accordance with the context in which the term is used. For example, the software can be machine code, firmware, embedded code, and application software. Also for example, the hardware can be circuitry, processor, computer, integrated circuit, integrated circuit cores, a pressure sensor, an inertial sensor, a microelectromechanical system (MEMS), passive devices, or a combination thereof.

Referring now to FIG. 1, therein is shown an electronic system 100 with a dynamic localization mechanism in an embodiment of the present invention. The electronic system 100 includes a first device 102, such as a client device, connected to a second device 106, such as a client device or server. The first device 102 can communicate with the second device 106 with a communication path 104, such as a wireless or wired connection.

For example, the first device 102 can be any of a variety of mobile devices. As a more specific example, the first device 102 can be any of a variety of mobile devices capable of being carried or held by the user such as a mobile phone. In addition, the first device 102 can be any of a variety of wearable devices, such as a watch, a health monitor, a fitness band, an electronic bracelet, a head-mounted device, a remote device, an electronic accessory, a fashion accessory, a diagnostic patch, an identification patch, a patch holder, or a combination thereof. As an additional example, the first device 102 can be a modular unit adapted to attach to or be housed in a wristband, an armband, a bracelet, a headset, an eyeglass frame, a head-mounted device, a virtual reality device, a pendant, a fashion accessory, a heart rate monitor strap, a shoe, a patch holder, or a combination thereof.

The first device 102 can be a standalone device or can be incorporated with a mobile device, an entertainment device, an article of clothing, an accessory, an adhesive device, a multi-functional device, or a combination thereof. The first device 102 can couple to the communication path 104 to communicate with the second device 106.

As shown in FIG. 1, the first device 102 can include a fastening unit 103. The fastening unit 103 is configured to secure the first device 102 to a human user or an object. For example, the fastening unit 103 can include a strap, a band, a clasp, a latch, a tie, a ring, a clip, or a combination thereof. As a more specific example, the fastening unit 103 can include a watch strap, a wristband, a bracelet clasp, an armband, a headband, a ring band, a pocket clip, an earpiece, an eyeglass frame, an eyewear holder, a necklace, or a combination thereof.

The fastening unit 103 can be constructed of a variety of materials. For example, the fastening unit 103 can be constructed of a polymeric material, an elastomeric material, a metallic material, a fabric, or a combination thereof. As will be discussed in the sections that follow, the fastening unit 103 can house a plurality of sensors for obtaining a contextual information concerning a usage environment or user, a device placement or attachment location, a biometric or physiological information, a physical movement of the user, or a combination thereof.

The second device 106 can be a mobile device or a non-mobile device. For example, the second device 106 can be any of a variety of mobile devices, such as a smartphone, a tablet device, a cellular phone, a personal digital assistant, a notebook computer, a netbook computer, a thin client device, a multi-functional mobile communication or entertainment device, or a combination thereof.

The second device 106 can also be a non-mobile device such as a computing device, an appliance, an internet of things (IoT) device, or a combination thereof. The second device 106 can be any of a variety of centralized or decentralized computing devices. For example, the second device 106 can be a desktop computer, a grid computing resource, a server, a server farm, a virtualized computing resource, a cloud computing resource, a router, a switch, a peer-to-peer distributed computing resource, or a combination thereof.

The second device 106 can be centralized in a single computer room, distributed across different rooms, distributed across different geographical locations, or embedded within a telecommunications network. For example, the second device 106 can be a particularized machine, such as a mainframe, a server, a cluster server, a rack mounted server, or a blade server, or as more specific examples, an IBM System z10™ Business Class mainframe or a HP ProLiant ML™ server.

For illustrative purposes, the electronic system 100 is described with the first device 102 as a wearable device, although it is understood that the second device 106 can also be a wearable device. The second device 106 can have a means for coupling with the communication path 104 to communicate with the first device 102.

Also for illustrative purposes, the electronic system 100 is shown with the second device 106 and the first device 102 as end points of the communication path 104, although it is understood that the electronic system 100 can have a different partition between the first device 102, the second device 106, and the communication path 104.

For example, the first device 102, the second device 106, or a combination thereof can also function as part of the communication path 104. As a more specific example, the first device 102 can be a watch-type device and the second device 106 can be a server. In this example, the first device 102 can connect directly to the second device 106 through the communication path 104. As an additional example, the first device 102 representing the watch-type device can connect to the server through a set of devices including the second device 106 such as a smartphone, a notebook, a desktop computer, or a combination thereof.

The communication path 104 can be a variety paths or connections. For example, the communication path 104 can include a wireless communication path, a wired communication path, an optical communication path, an ultrasonic communication path, or a combination thereof. Wireless communication paths can include satellite communication, cellular communication, Bluetooth™, Bluetooth™ Low Energy (BLE), wireless High-Definition Multimedia Interface (HDMI), ZigBee™, Near Field Communication (NFC), Infrared Data Association standard (IrDA), wireless fidelity (WiFi), worldwide interoperability for microwave access (WiMAX), or a combination thereof. Wired communication paths can include Ethernet, HDMI, digital subscriber line (DSL), fiber to the home (FTTH), plain old telephone service (POTS), or a combination thereof.

Fluid mediums including gases, liquid, or solids can be examples of communication paths for ultrasonic or other high frequency acoustic communication. An example of a fluid medium is air molecules capable of being displaced by a mechanical wave such as a compression wave.

Further, the communication path 104 can traverse a number of network topologies and distances. For example, the communication path 104 can include a direct connection, personal area network (PAN), local area network (LAN), metropolitan area network (MAN), wide area network (WAN) or any combination thereof.

Figure 2:
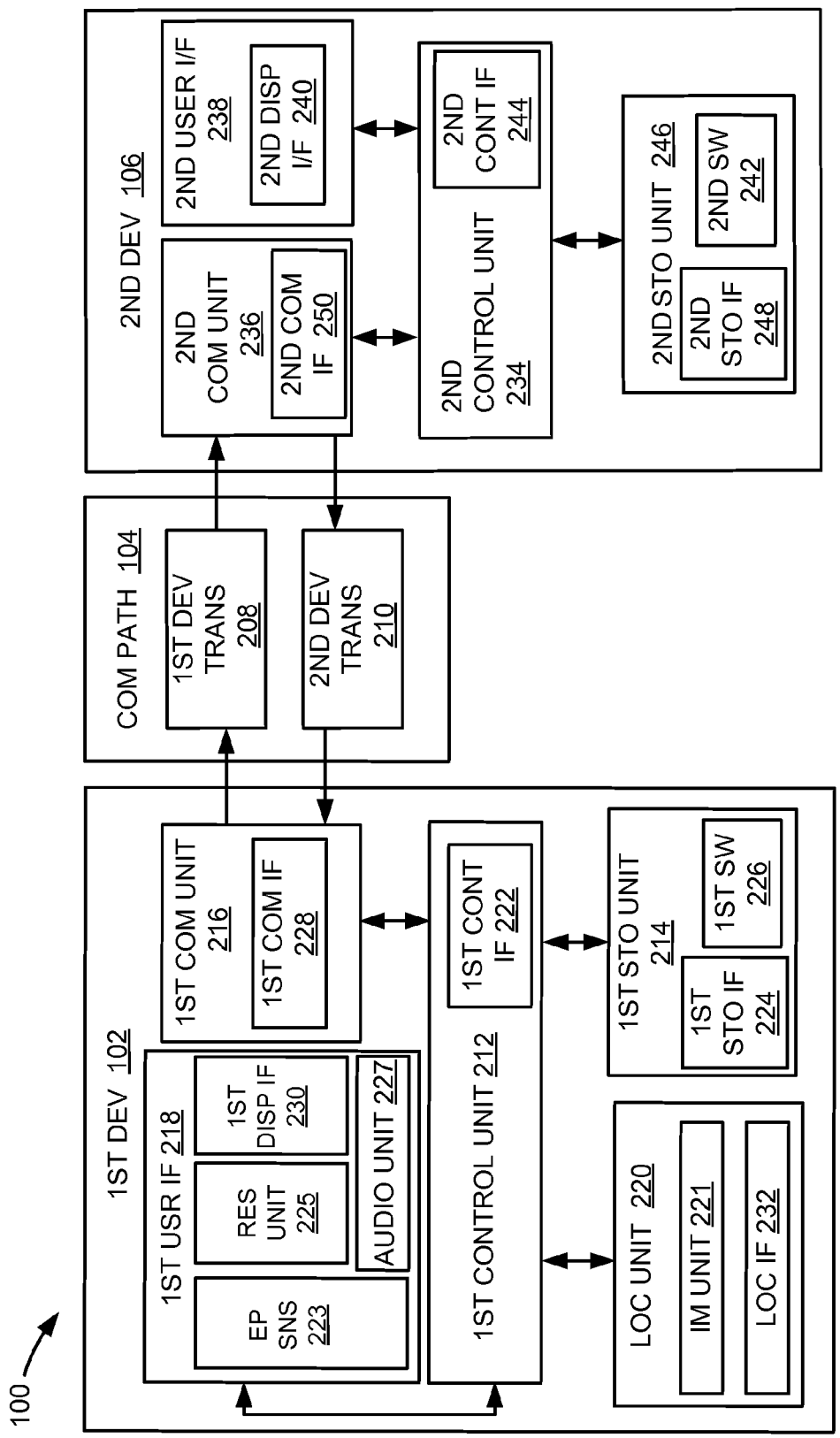
FIG. 2 is an exemplary block diagram of the electronic system.

Referring now to FIG. 2 therein is shown an exemplary block diagram of the electronic system 100. The electronic system 100 can include the first device 102, the communication path 104, and the second device 106. The first device 102 can send information in a first device transmission 208 over the communication path 104 to the second device 106. The second device 106 can send information in a second device transmission 210 over the communication path 104 to the first device 102.

For illustrative purposes, the electronic system 100 is shown with the first device 102 as a client device, although it is understood that the electronic system 100 can have the first device 102 as a different type of device. Also for illustrative purposes, the electronic system 100 is shown with the second device 106 as a mobile device, a computing device, or a combination thereof, although it is understood that the electronic system 100 can have the second device 106 as a different type of device.

Embodiments of the present invention are not limited to this selection for the type of devices. The selection is an example of the embodiments of the present invention.

The first device 102 can include a first control unit 212, a first storage unit 214, a first communication unit 216, a first user interface 218, and a location unit 220. The first control unit 212 can include a first control interface 222. The first control unit 212 can execute a first software 226 to provide the intelligence of the electronic system 100. The first control unit 212 can be implemented in a number of different manners.

For example, the first control unit 212 can be a processor, an embedded processor, a microprocessor, a hardware control logic, a hardware finite state machine (FSM), a digital signal processor (DSP), or a combination thereof. The first control interface 222 can be used for communication between the first control unit 212 and other functional units in the first device 102. The first control interface 222 can also be used for communication that is external to the first device 102.

The first control interface 222 can receive information from the other functional units or from external sources, or can transmit information to the other functional units or to external destinations. The external sources and the external destinations refer to sources and destinations external to the first device 102.

The first control interface 222 can be implemented in different ways and can include different implementations depending on which functional units or external units are being interfaced with the first control interface 222. For example, the first control interface 222 can be implemented with a pressure sensor, an inertial sensor, a microelectromechanical system (MEMS), optical circuitry, waveguides, wireless circuitry, wireline circuitry, or a combination thereof.

The location unit 220 can generate a location and movement information, including a geographic position, a heading, an inertial orientation, a speed, or a combination thereof or a change therein of the first device 102. The location unit 220 can include an inertial measurement unit 221. The inertial measurement unit 221 can generate an inertial information related to the first device 102. For example, the inertial measurement unit 221 can generate information concerning a linear acceleration, an angular acceleration, or a combination thereof of the first device 102. The inertial measurement unit 221 can include an accelerometer, a gyroscope, or a combination thereof.

The location unit 220 can be implemented in many ways. For example, the location unit 220 can function as at least a part of a global positioning system (GPS), an inertial navigation system, a magnetometer, a compass, a spectrum analyzer, a beacon, a cellular-tower location system, a pressure location system, or any combination thereof. In addition, the inertial measurement unit 221 can be implemented as a multi-axis accelerometer including a three-axis accelerometer, a multi-axis gyroscope including a three-axis MEMS gyroscope, or a combination thereof.

The location unit 220 can include a location interface 232. The location interface 232 can be used for communication between the location unit 220 and other functional units in the first device 102. The location interface 232 can also be used for communication that is external to the first device 102.

The location interface 232 can receive information from the other functional units or from external sources, or can transmit information to the other functional units or to external destinations. The external sources and the external destinations refer to sources and destinations external to the first device 102.

The location interface 232 can include different implementations depending on which functional units or external units are being interfaced with the location unit 220. The location interface 232 can be implemented with technologies and techniques similar to the implementation of the first control interface 222.

The first storage unit 214 can store the first software 226. The first storage unit 214 can also store relevant information, such as advertisements, biometric information, points of interest (POIs), navigation routing entries, reviews/ratings, feedback, or any combination thereof.

The first storage unit 214 can be a volatile memory, a nonvolatile memory, an internal memory, an external memory, or a combination thereof. For example, the first storage unit 214 can be a nonvolatile storage such as non-volatile random access memory (NVRAM), Flash memory, disk storage, or a volatile storage such as static random access memory (SRAM).

The first storage unit 214 can include a first storage interface 224. The first storage interface 224 can be used for communication between the location unit 220 and other functional units in the first device 102. The first storage interface 224 can also be used for communication that is external to the first device 102.

The first storage interface 224 can receive information from the other functional units or from external sources, or can transmit information to the other functional units or to external destinations. The external sources and the external destinations refer to sources and destinations external to the first device 102.

The first storage interface 224 can include different implementations depending on which functional units or external units are being interfaced with the first storage unit 214. The first storage interface 224 can be implemented with technologies and techniques similar to the implementation of the first control interface 222.

The first communication unit 216 can enable external communication to and from the first device 102. For example, the first communication unit 216 can permit the first device 102 to communicate with the second device 106 of FIG. 1, an attachment, such as a peripheral device or a notebook computer, and through the communication path 104.

The first communication unit 216 can also function as a communication hub allowing the first device 102 to function as part of the communication path 104 and not limited to be an end point or terminal unit to the communication path 104. The first communication unit 216 can include active and passive components, such as microelectronics or an antenna, for interaction with the communication path 104.

The first communication unit 216 can include a first communication interface 228. The first communication interface 228 can be used for communication between the first communication unit 216 and other functional units in the first device 102. The first communication interface 228 can receive information from the other functional units or can transmit information to the other functional units.

The first communication interface 228 can include different implementations depending on which functional units are being interfaced with the first communication unit 216. The first communication interface 228 can be implemented with technologies and techniques similar to the implementation of the first control interface 222.

The first user interface 218 allows a user (not shown) to interface and interact with the first device 102. The first user interface 218 can include an input device and an output device. Examples of the input device of the first user interface 218 can include a keypad, a touchpad, soft-keys, a keyboard, an electric potential sensor 223, a response unit 225, an audio unit 227, or any combination thereof to provide data and communication inputs. Examples of the output device of the first user interface 218 can include the response unit 225, the audio unit 227, the first display interface 230, or any combination thereof to provide data and communication outputs.

The electric potential sensor 223 can measure an electric charge or electrical potential difference. The electric potential sensor 223 can include an electrode. The electrode can be an interface of the electric potential sensor 223 for obtaining an electrical signal from a measurement subject. The electrode can include a non-contact electrode, a contact electrode such as a dry electrode or a wet electrode, or a combination thereof. For example, the non-contact electrode can include a printed circuit board having an impedance amplifier, an analog-to-digital converter, a capacitor, a shield component, or a combination thereof.

The electric potential sensor 223 can measure an electrical bio-potential signal such as an electroencephalography (EEG) signal, an electrocardiograph (ECG) signal, an electromyography (EMG) signal, an electrooculargraph (EOG) signal, or a combination thereof. In addition, the electric potential sensor 223 can measure small changes in the ambient electric field as evidenced by changes in the impedance detected by the electric potential sensor 223. The electric potential sensor 223 can use such changes in the ambient electric field to determine a change in the proximity or spatial position of dielectric objects such as parts of a human body.

The electric potential sensor 223 can be implemented as wireline circuitry, wireless circuitry, an integrated circuit, a chipset, a sensor array, or a combination thereof.

For illustrative purposes, the electric potential sensor 223 is shown as being housed in the first device 102. However, it is understood that the electric potential sensor 223 can operate on the periphery or outside of the first device 102. For example, one or more instances of the electric potential sensor 223 can be enclosed in the fastening unit 103 of the first device 102.

The response unit 225 is configured to detect a physical interaction with an object or person and to produce a physical stimulus such as a vibration or haptic feedback. The response unit 225 can include a capacitive sensor including capacitive cells or conductor plates, a resistive sensor, a piezoelectric sensor including a piezoresistive sensor or a piezocapacitive sensor, an acoustic sensor including a surface acoustic wave sensor, a transducer or actuator component, a pressure sensor, or a combination thereof. The response unit 225 can be implemented as a wireline circuitry, wireless circuitry, an integrated circuit, a chipset, a sensor array, or a combination thereof.

For illustrative purposes, the response unit 225 is shown as being housed in the first device 102. However, it is understood that the response unit 225 can operate on the periphery or outside of the first device 102. For example, one or more instances of the response unit 225 can be enclosed in the fastening unit 103 of the first device 102.

The audio unit 227 is configured to capture or produce an acoustic signal. The audio unit 227 can include a speaker and a microphone including a condenser microphone, a piezoelectric microphone, a dynamic microphone, or a combination thereof. For illustrative purposes, the audio unit 227 is shown as being housed in the first device 102. However, it is understood that the audio unit 227 can operate on the periphery or outside of the first device 102.

The first user interface 218 can also include a first display interface 230. The first display interface 230 can include a liquid crystal display (LCD), a light emitting diode (LED) display such as an organic light emitting diode (OLED), an active matrix organic light emitting diode (AMOLED) display or a Super AMOLED display, a projector, a video screen, or any combination thereof.

The first control unit 212 can operate the first user interface 218 to display information generated by the electronic system 100. The first control unit 212 can also execute the first software 226 for the other functions of the electronic system 100, including receiving location information from the location unit 220. The first control unit 212 can further execute the first software 226 for interaction with the communication path 104 via the first communication unit 216.

The second device 106 can be optimized for implementing the various embodiments in a multiple device embodiment with the first device 102. The second device 106 can provide the additional or higher performance processing power compared to the first device 102. The second device 106 can include a second control unit 234, a second communication unit 236, and a second user interface 238.

The second user interface 238 allows the user to interface and interact with the second device 106. The second user interface 238 can include an input device and an output device. Examples of the input device of the second user interface 238 can include a keypad, a touchpad, soft-keys, a keyboard, a microphone, or any combination thereof to provide data and communication inputs. Examples of the output device of the second user interface 238 can include a second display interface 240. The second display interface 240 can include a display, a projector, a video screen, a speaker, or any combination thereof.

The second control unit 234 can execute a second software 242 to provide the intelligence of the second device 106 of the electronic system 100. The second software 242 can operate in conjunction with the first software 226. The second control unit 234 can provide additional performance compared to the first control unit 212.

The second control unit 234 can operate the second user interface 238 to display information. The second control unit 234 can also execute the second software 242 for the other functions of the electronic system 100, including operating the second communication unit 236 to communicate with the first device 102 over the communication path 104.

The second control unit 234 can be implemented in a number of different manners. For example, the second control unit 234 can be a processor, an embedded processor, a microprocessor, a hardware control logic, a hardware finite state machine (FSM), a digital signal processor (DSP), or a combination thereof.

The second control unit 234 can include a second controller interface 244. The second controller interface 244 can be used for communication between the second control unit 234 and other functional units in the second device 106. The second controller interface 244 can also be used for communication that is external to the second device 106.

The second controller interface 244 can receive information from the other functional units or from external sources, or can transmit information to the other functional units or to external destinations. The external sources and the external destinations refer to sources and destinations external to the second device 106.

The second controller interface 244 can be implemented in different ways and can include different implementations depending on which functional units or external units are being interfaced with the second controller interface 244. For example, the second controller interface 244 can be implemented with a pressure sensor, an inertial sensor, a microelectromechanical system (MEMS), optical circuitry, waveguides, wireless circuitry, wireline circuitry, or a combination thereof.

A second storage unit 246 can store the second software 242. The second storage unit 246 can also store the relevant information, such as advertisements, biometric information, points of interest, navigation routing entries, reviews/ratings, feedback, or any combination thereof. The second storage unit 246 can be sized to provide the additional storage capacity to supplement the first storage unit 214.

For illustrative purposes, the second storage unit 246 is shown as a single element, although it is understood that the second storage unit 246 can be a distribution of storage elements. Also for illustrative purposes, the electronic system 100 is shown with the second storage unit 246 as a single hierarchy storage system, although it is understood that the electronic system 100 can have the second storage unit 246 in a different configuration. For example, the second storage unit 246 can be formed with different storage technologies forming a memory hierarchal system including different levels of caching, main memory, rotating media, or off-line storage.

The second storage unit 246 can be a volatile memory, a nonvolatile memory, an internal memory, an external memory, or a combination thereof. For example, the second storage unit 246 can be a nonvolatile storage such as non-volatile random access memory (NVRAM), Flash memory, disk storage, or a volatile storage such as static random access memory (SRAM).

The second storage unit 246 can include a second storage interface 248. The second storage interface 248 can be used for communication between the location unit 220 and other functional units in the second device 106. The second storage interface 248 can also be used for communication that is external to the second device 106.

The second storage interface 248 can receive information from the other functional units or from external sources, or can transmit information to the other functional units or to external destinations. The external sources and the external destinations refer to sources and destinations external to the second device 106.

The second storage interface 248 can include different implementations depending on which functional units or external units are being interfaced with the second storage unit 246. The second storage interface 248 can be implemented with technologies and techniques similar to the implementation of the second controller interface 244.

The second communication unit 236 can enable external communication to and from the second device 106. For example, the second communication unit 236 can permit the second device 106 to communicate with the first device 102 over the communication path 104.

The second communication unit 236 can also function as a communication hub allowing the second device 106 to function as part of the communication path 104 and not limited to be an end point or terminal unit to the communication path 104. The second communication unit 236 can include active and passive components, such as microelectronics or an antenna, for interaction with the communication path 104.

The second communication unit 236 can include a second communication interface 250. The second communication interface 250 can be used for communication between the second communication unit 236 and other functional units in the second device 106. The second communication interface 250 can receive information from the other functional units or can transmit information to the other functional units.

The second communication interface 250 can include different implementations depending on which functional units are being interfaced with the second communication unit 236. The second communication interface 250 can be implemented with technologies and techniques similar to the implementation of the second controller interface 244.

The first communication unit 216 can couple with the communication path 104 to send information to the second device 106 in the first device transmission 208. The second device 106 can receive information in the second communication unit 236 from the first device transmission 208 of the communication path 104.

The second communication unit 236 can couple with the communication path 104 to send information to the first device 102 in the second device transmission 210. The first device 102 can receive information in the first communication unit 216 from the second device transmission 210 of the communication path 104. The electronic system 100 can be executed by the first control unit 212, the second control unit 234, or a combination thereof.

For illustrative purposes, the second device 106 is shown with the partition having the second user interface 238, the second storage unit 246, the second control unit 234, and the second communication unit 236, although it is understood that the second device 106 can have a different partition. For example, the second software 242 can be partitioned differently such that some or all of its function can be in the second control unit 234 and the second communication unit 236. Also, the second device 106 can include other functional units not shown in FIG. 3 for clarity.

The functional units in the first device 102 can work individually and independently of the other functional units. The first device 102 can work individually and independently from the second device 106 and the communication path 104.

The functional units in the second device 106 can work individually and independently of the other functional units. The second device 106 can work individually and independently from the first device 102 and the communication path 104.

For illustrative purposes, the electronic system 100 is described by operation of the first device 102 and the second device 106. It is understood that the first device 102 and the second device 106 can operate any of the modules and functions of the electronic system 100. For example, the first device 102 is described to operate the location unit 220, although it is understood that the second device 106 can also operate the location unit 220.

Figure 3:
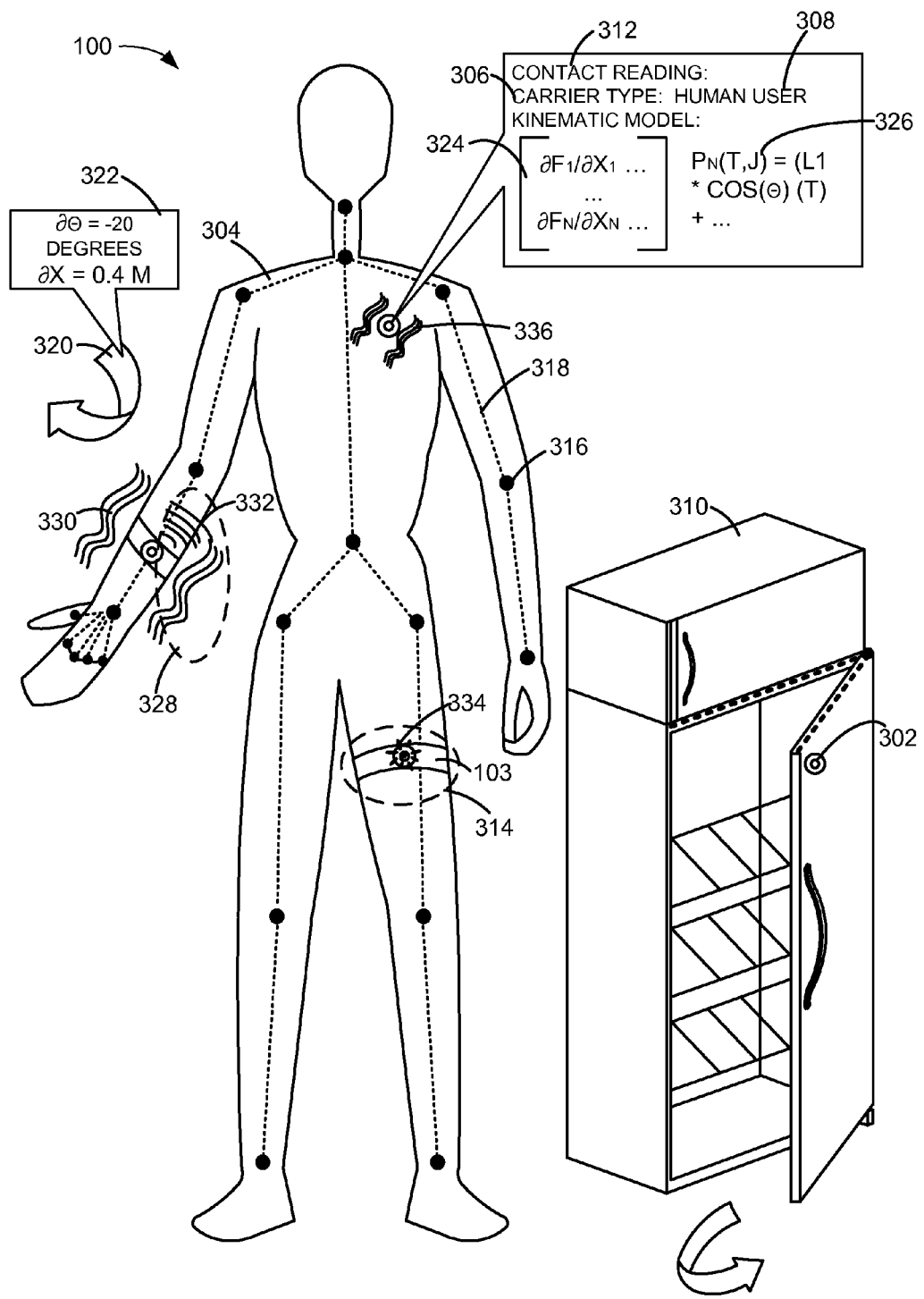
FIG. 3 is an example diagram of an attachable device of the electronic system attached to a carrier.

Referring now to FIG. 3, therein is shown an example diagram of an attachable device 302 of the electronic system 100 attached to a carrier 304. The carrier 304 can include a person, an animal, an object, or a combination thereof with the attachable device 302 attached thereto. The carrier 304 can also include a subject or an object for monitoring or sending.

For clarity and brevity, the discussion of an embodiment of the electronic system 100 will be described with the attachable device 302 representing the first device 102 of FIG. 1. However, it is understood that the attachable device 302 can also be represented using the second device 106 of FIG. 1.

The attachable device 302 is an electronic device configured to be affixed to or carried by the carrier 304. For example, the carrier 304 can be categorized by a carrier type 306 such as the human user 308 or the object 310. The human user 308 can be a user of the electronic system 100.

The object 310 can include an apparatus or a fixture including at least one moveable part. The object 310 can be configured to receive the attachable device 302 for attaching to the moveable part. For example, the object 310 can include an appliance such as a refrigerator, an oven, or a washing machine; a fixture such as a window, a gate, or a door; a piece of equipment such as an exercise equipment or other mechanical equipment; or a combination thereof.

As will be discussed in the sections below, the electronic system 100 can determine the carrier type 306 based on a contact reading 312 obtained through the attachable device 302. The contact reading 312 is a measurement of a physical or physiological characteristic of the carrier 304. For example, the contact reading 312 can include a conductance, impedance, or resistance measurement of a biological or non-biological surface or material. As a more specific example, the contact reading 312 can include a galvanic skin response or a surface conductance.

When the attachable device 302 is affixed to or worn by the human user 308, the attachable device 302 can be used as a wearable device such as a watch, a health monitor, a fitness band, an electronic bracelet, a head-mounted device, a fashion accessory, a patch holder, or a combination thereof. Moreover, in cases where the carrier 304 is the object 310, the attachable device 302 can be used as an activity monitor or motion detector. For example, the attachable device 302 can be affixed to a door of a refrigerator to monitor the number of times the door opens.

The attachable device 302 can be affixed to or carried by the carrier 304 at an attachment location 314. The attachment location 314 is a site or locus on the carrier 304 for having the attachable device 302 affixed thereto or for housing the attachable device 302. For example, the carrier 304 can be the human user 308 and the attachable device 302 can be used as an exercise band having the fastening unit 103. In this example, the attachment location 314 for the attachable device 302 can include a wrist, an arm, or a leg of the human user 308 when the attachable device 302 is attached to the human user 308 using the fastening unit 103.

The attachable device 302 can also be carried by the carrier 304 at the attachment location 314. For example, when the attachable device 302 is a mobile phone, a mobile music player, a tablet device, or a combination thereof, the attachment location 314 can include a location-specific compartment of the carrier 304 such as a pocket or holder.

The attachment location 314 can include a joint 316, a joint segment 318, or a combination thereof. The joint segment 318 is a representation of an appendage or part of the carrier 304 capable of being articulated or moved by the joint 316. The joint segment 318 can include a representation of a limb, a body portion, or a combination thereof. In addition, the joint segment 318 can include a representation of a mechanical arm, an equipment or apparatus part, a fixture part, a machine part, or a combination thereof.

The joint 316 is a representation of a structure of the carrier 304 configured to articulate the joint segment. When the carrier 304 is a biological organism, the joint 316 can refer to a tissue structure for connecting two or more bone segments. For example, the joint 316 can include a ball-and-socket joint, a hinge joint, or a pivot joint. When the carrier 304 is the object 310, the joint 316 can refer to a mechanical structure for connecting two instances of the joint segment 318.

The joint 316 can articulate the joint segment 318 to cause a motion 320. The motion 320 is a representation of a spatial displacement or movement of carrier 304 or a portion thereof. The motion 320 can correspond to a movement of the joint segment 318. The motion 320 can be made by the carrier 304 while the carrier 304 remains in place or undertakes a geographic displacement relative to a fixed location or coordinate. For example, when the carrier 304 is the human user 308 the motion can include an arm flexion motion, a leg extension motion, a foot pronation motion, or a combination thereof.

As will be discussed in the sections below, the electronic system 100 can capture a motion profile 322 of the motion 320 using data obtained by the attachable device 302. The motion profile 322 is a geospatial data or movement data or information concerning the motion 320. The electronic system 100 can capture the motion profile 322 by collecting or sampling coordinates, geographic positions, proximity signals, or orientation angles of the attachable device 302 over time.

The electronic system 100 can determine the attachment location 314 of the attachable device 302 by determining and analyzing a kinematic model 324. The kinematic model 324 is a quantitative representation of possible motions or movements made by a subject. For example, the kinematic model 324 can be a quantitative representation of possible motions or movements made by the carrier 304.

The kinematic model 324 can include equations, matrices, functions, or relationships for representing kinematic properties or constraints. The kinematic model 324 can also include a joint-specific equation 326. The joint-specific equation 326 is an equation, function, or relationship for representing the motion 320 of the carrier 304 or a portion therein. The joint-specific equation 326 can represent the motion 320 of the joint segment 318, the joint 316, or a combination thereof for the carrier 304. For example, the joint-specific equation 326 can represent the motion 320 of the joint segment 318 caused by the joint 316. As a more specific example, the joint-specific equation 326 can include equations or functions pertaining to the constraints or properties of a biological joint or physical joint.

As shown in FIG. 3, the attachable device 302 can generate an adjustable feedback 328, a positioning feedback 336, or a combination thereof. The adjustable feedback 328 is a stimulus generated by the attachable device 302 for interacting or communicating with the carrier 304. The adjustable feedback 328 can include a haptic feedback 330, an audio feedback 332, a visual feedback 334, or a combination thereof.

The haptic feedback 330 refers to a mechanical stimulus for communicating or interacting with the carrier 304. The haptic feedback 330 can include a physical displacement, a generated force, or a combination thereof capable of being perceived by the carrier 304. For example, the electronic system 100 can use an actuator of the response unit 225 to generate the haptic feedback 330. Also, for example, the haptic feedback 330 can be perceived or physically felt on a body part of the human user 308. As an additional example, the haptic feedback 330 can be perceived by the object 310 using a vibration sensor or a physical sensor for sensing force.

The audio feedback 332 is an auditory stimulus capable of being perceived by the carrier 304. The electronic system 100 can use the audio unit 227 to generate the audio feedback 332. The visual feedback 334 refers to a visual stimulus capable of being perceived by the carrier 304. The electronic system 100 can use the first display interface 230 or a portion therein to generate the visual feedback 334.

The positioning feedback 336 is a stimulus generated by the attachable device 302 for guiding the carrier 304 or another user of the electronic system 100 to move the attachable device 302 from one instance of the attachment location 314 to another instance of the attachment location 314. As will be discussed in the sections below, the electronic system 100 can guide the carrier 304 or another user of the electronic system 100 to move the attachable device 302 using the positioning feedback 336 by generating the positioning feedback 336 until the attachable device 302 is moved to a new instance of the attachment location.

Figure 4:
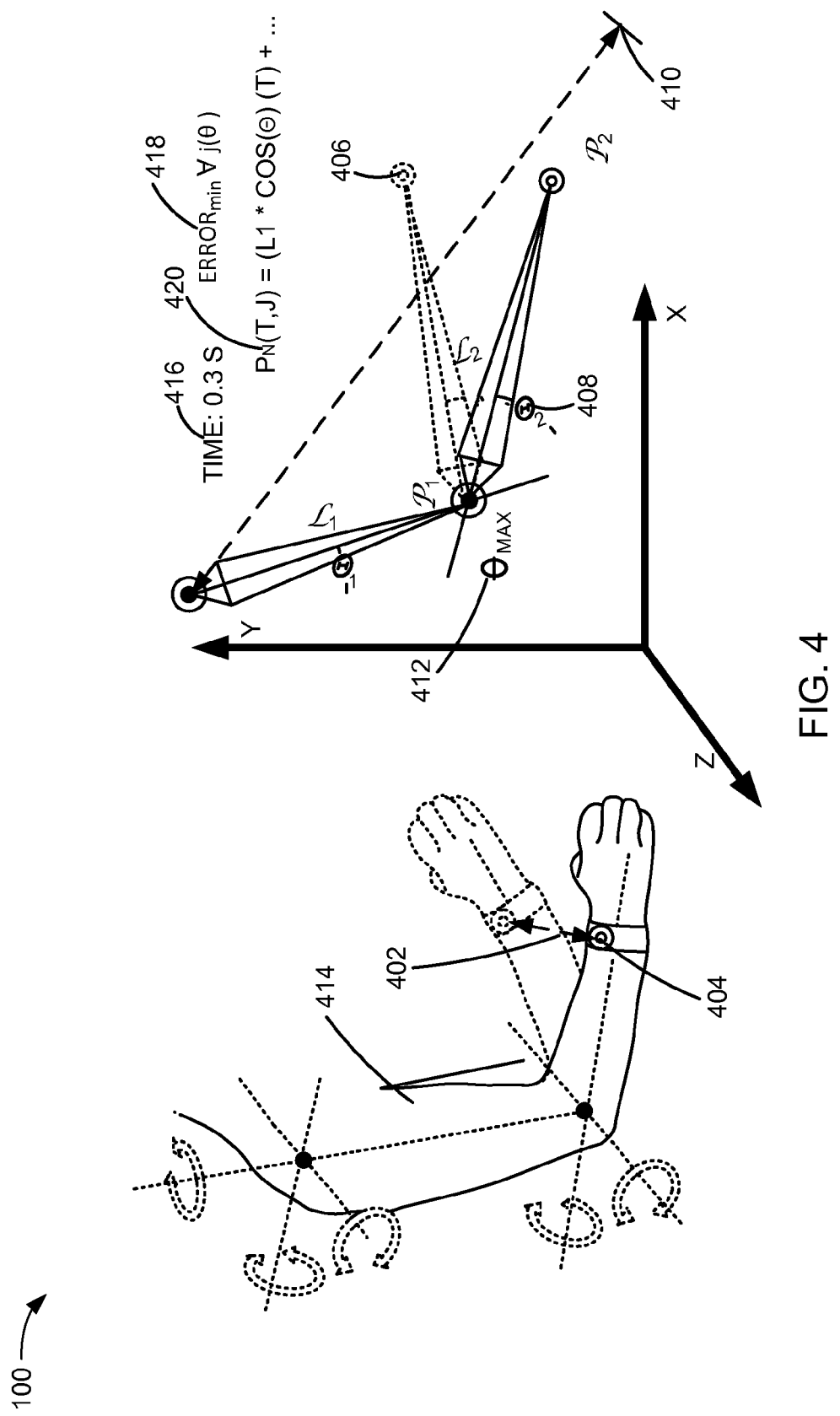
FIG. 4 is an example diagram of the carrier undertaking a motion.

Referring now to FIG. 4, there is shown an example diagram of the carrier 304 of FIG. 3 undertaking an instance of the motion 320 of FIG. 3. As shown in FIG. 4, the motion 320 can involve a displacement change 402, an orientation change 408, or a combination thereof.

The displacement change 402 is a change in a geographic position of the attachable device 302 of FIG. 3. The displacement change 402 can be measured based on a vector difference between a final instance of a measured spatial position 404 and an initial instance of the measured spatial position 404.

The displacement change 402 can further be measured relative to a fixed coordinate system, a known reference point, such as a user or a landmark, or a combination thereof. The measured spatial position 404 is a geographic position of the attachable device 302 relative to a fixed coordinate. For example, the electronic system 100 can measure the displacement change 402 as an Euclidean distance or a scale-invariant distance.

The orientation change 408 is a change in a spatial alignment or a movement along a relative axis of the attachable device 302. The orientation change 408 can be measured based on one or more axes relative to the attachable device 302 or a reference point known to the electronic system 100. The orientation change 408 can represent a degree difference between orientation angles relative to the one or more axes. For example, the orientation change 408 can be represented by a change in a yaw angle, a pitch angle, a roll angle, or a combination thereof.

As shown in FIG. 4, the displacement change 402 can be limited by distance constraints 410 within a detection period 416. In addition, the orientation change 408 can be limited by angular constraints 412 within the same or a different instance of the detection period 416. The distance constraints 410 can refer to a maximum change in a spatial position of a measured device or entity within the detection period 416. The detection period 416 is a time duration for measuring the motion 320.

The distance constraints 410 can be recognized by the electronic system 100 and can be based on a length of the joint segment 318 of FIG. 3, a length of a body portion, or a combination thereof. In addition, the angular constraints 412 can be imposed by a degree-of-freedom of the joint 316 of FIG. 3 articulating the joint segment 318.

The distance constraints 410, the angular constraints 412, or a combination thereof can be determined based on a mechanical model or an anatomical model 414 of the carrier 304. The mechanical model refers to a representation of the mechanical structure of the object 310 of FIG. 3. For example, the mechanical model can include information on the angular constraints 412 or distance constraints 410 imposed on the motion 320 of a door articulated by a hinged joint.

The anatomical model 414 is a representation of the morphology and structure of the human body. For example, the anatomical model 414 can include information on the angular constraints 412 or distance constraints 410 imposed on the motion 320 of a forearm articulated by an elbow joint.

As will be discussed in detail in the sections below, the electronic system 100 can determine the attachment location 314 of FIG. 3 by determining the joint segment 318 articulated by the joint 316. The electronic system 100 can determine the joint segment 318 by matching the motion 320 of the attachable device 302 with the motion 320 of the joint segment 318 represented by equations, functions, or relationships included as part of the kinematic model 324 of FIG. 3.

In addition, the electronic system 100 can determine the attachment location 314 based on a closed form solution 420. The closed form solution 420 is an expression or formula that can be evaluated in a finite number of standard operations. For example, the electronic system 100 can determine the attachment location 314 based on the closed form solution 420 by determining an expression or set of operations that can mimic the motion 320 of the joint segment 318.

The electronic system 100 can also use an inverse kinematic solver 418 to determine the identity of the joint 316 causing the motion 320 of the joint segment 318. The inverse kinematic solver 418 is a method of determining the identity of the joint 316 based on a comparison of a measured motion data with a modeled motion data involving the joint segment 318. The measured motion data can include the measured spatial position 404 and the modeled motion data can include a modeled spatial position 406.

The modeled spatial position 406 is a relative geographic position of the attachable device 302 determined by the electronic system 100 based on the kinematic model 324. The modeled spatial position 406 can be a geographic position of the attachable device 302 relative to a fixed coordinate or location. For example, the electronic system 100 can apply data concerning the orientation change 408, the displacement change 402, or a combination thereof to determine the modeled spatial position 406.

Figure 5:
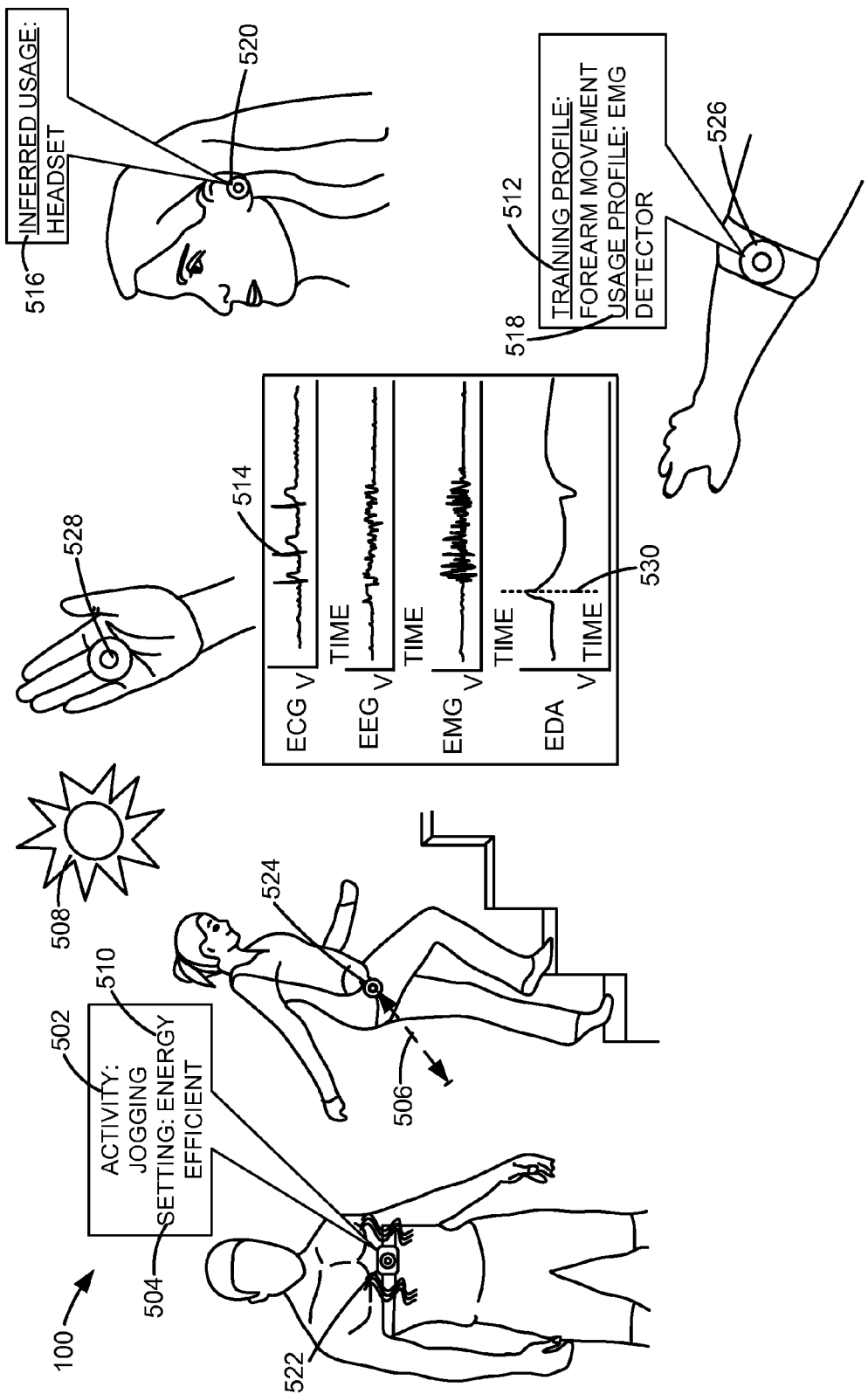
FIG. 5 is an example diagram of the carrier undertaking an activity.

Referring now to FIG. 5, therein is shown an example diagram of the carrier 304 of FIG. 3 undertaking an activity 502. The activity 502 can be a classification of bodily movements or mechanical movements undertaken by the carrier 304 and involving the motion 320 of FIG. 3. For example, the activity 502 can refer to a task involving multiple instances of the motion 320.

The activity 502 can be classified based on an amount of movement such as an ambulatory activity or a sedentary activity. In addition, the activity 502 can be classified by a purpose of the activity 502 such as a work activity or an exercise activity. Moreover, the activity 502 can include common bodily movements including walking or jogging.

As will be discussed in the sections below, the electronic system 100 can determine the activity 502 based on the motion profile 322 of FIG. 3, the carrier type 306 of FIG. 3, a training profile 512, or a combination thereof. The training profile 512 includes geospatial or motion data concerning the activity 502. The training profile 512 can initially be predetermined by the electronic system 100 and updated based on additional geospatial or motion data obtained by the attachable device 302 of FIG. 3.

The electronic system 100 can determine an inferred usage 516 of the attachable device 302. The inferred usage 516 is a possible utilization of or a purpose intended by the user for the attachable device 302 deduced by the electronic system 100. The electronic system 100 can determine the inferred usage 516 based on the attachment location 314 of FIG. 3, a usage context 508, a usage profile 518, or a combination thereof.

The usage context 508 is a set of circumstances or conditions surrounding the usage of the attachable device 302. For example, the usage context 508 can include a usage time such as a time-of-day or day-of-the-week, an environmental context such as whether the usage occurred indoors or outdoors, a usage location, or a combination thereof.

The usage profile 518 refers to data or information concerning possible utilizations of the attachable device 302. For example, the attachable device 302 can be provisioned and used as a headset 520, an activity tracker 524, a heart rate monitor 522, an electromyography detector 526, an electrodermal activity detector 528, or a combination thereof. In each case, the usage profile 518 for such use can include information concerning the usage context 508 and a preferred instance of the attachment location 314 for the attachable device 302.

For example, the attachable device 302 can be used as the headset 520 when the attachment location 314 is located near an ear of the human user 308 and the attachable device 302 detects sound coming from the human user 308. As an additional example, the attachable device 302 can be used as the activity tracker 524 for tracking a distance traveled by the carrier 304 when the attachment location 314 is located on a hip or waist region of the human user 308 and the attachable device 302 detects a device movement 506.

The device movement 506 refers to a change in the geographical location or coordinates of the attachable device 302 above a threshold amount. For example, the device movement 506 can be any change in the geographical location of the attachable device 302 greater than 10 meters.

The attachable device 302 can also be used as the heart rate monitor 522, the electromyography detector 526, the electrodermal activity detector 528, or a combination thereof to track a biometric indicator 514. The biometric indicator 514 is a vital sign or a physical attribute of the human user 308 of FIG. 3.

For example, the biometric indicator 514 can include an electromyography signal including a surface electromyography signal for tracking an electrical activity of a muscle of the human user 308 and an electrodermal activity signal for tracking a stress level of the human user 308.

The attachable device 302 can be used as the electromyography detector 526 when the attachment location 314 is a forearm of the human user 308. In addition, the attachable device 302 can be used as the electrodermal activity detector 528 when the attachment location 314 is a hand of the human user 308.

The electronic system 100 can also generate a biometric marker 530 for detecting an instance of the biometric indicator 514 falling outside a threshold or acceptable range. The biometric marker 530 can include an upper or lower signal threshold for a physiological signal. The biometric marker 530 can be generated based on the attachment location 314. As a more specific example, the biometric marker 530 can be a heart rate above 160 beats per minute.

As will be discussed in the sections below, the electronic system 100 can generate a device setting 504 based on the attachment location 314. The device setting 504 is an operation mode of the attachable device 302 for interacting with the carrier 304, a user, or another device of the electronic system 100.

The electronic system 100 can generate the device setting 504 by generating an energy saving setting 510. The energy saving setting 510 is an operational mode for reducing an energy consumption of the attachable device 302. For example, the electronic system 100 can generate the energy saving setting 510 by enabling or disabling certain hardware components and software components.

Figure 6:
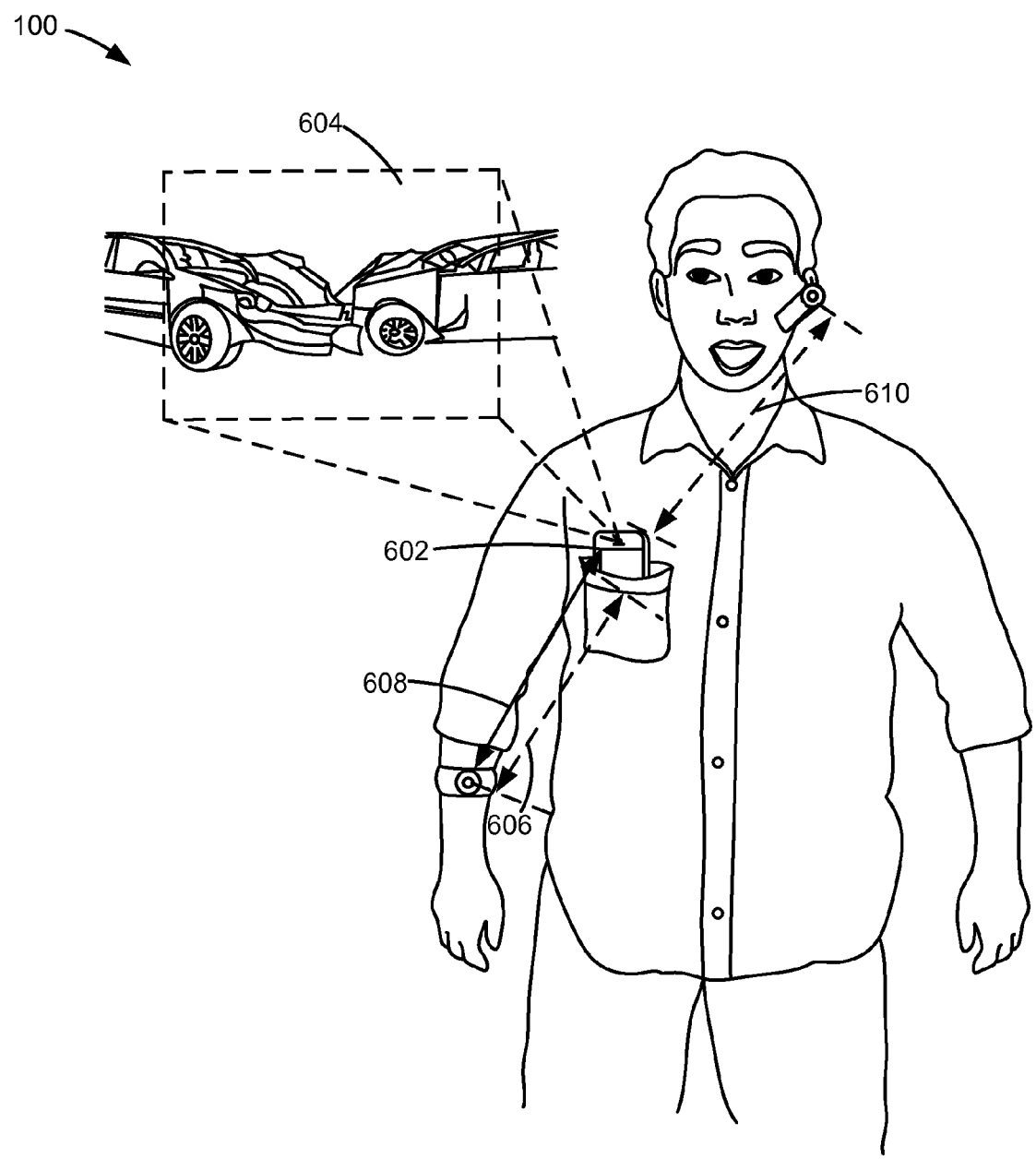
FIG. 6 is an example diagram of the attachable device interacting with a further device.

Referring now to FIG. 6, therein is shown an example diagram of the attachable device 302 of FIG. 3 interacting with a further device 602. For clarity and brevity, the further device 602 can be the first device 102 of FIG. 1, the second device 106 of FIG. 1, or a combination thereof. The further device 602 is an electronic device configured to connect and interact with the attachable device 302.

For example, the further device 602 can include a mobile computing device, such as a smartphone, tablet device, or notebook; a consumer electronic device having a network capability such as a television, a clock, or an audio system; an appliance having a network capability, such as a lighting unit, a thermostat, a washing machine, or a refrigerator; or a combination thereof. The attachable device 302 can communicate with the further device 602 through the communication path 104 of FIG. 1.

As will be discussed in the sections below, the electronic system 100 can determine a collaboration context 604 when the further device 602 is identified. The collaboration context 604 refers to a set of circumstances or conditions surrounding an interaction between the attachable device 302 and the further device 602. The collaboration context 604 can include a usage time, a usage location, an environmental context, or a combination thereof when the further device 602 is identified by the electronic system 100.

The collaboration context 604 can also include information concerning a collaboration arrangement 606. The collaboration arrangement 606 is a physical arrangement of the attachable device 302 and the further device 602 relative to the carrier 304 of FIG. 3. When the further device 602 is another instance of the attachable device 302, the electronic system 100 can determine the collaboration arrangement 606 based on the attachment location 314 of FIG. 3.

As will be discussed in the sections below, the electronic system 100 can generate a connection setting 608 based on the collaboration context 604, a preferred arrangement 610, or a combination thereof. The connection setting 608 is an operational mode of the attachable device 302 for interacting with the further device 602. The electronic system 100 can generate the connection setting 608 for enhancing a functionality of the attachable device 302 based on the presence of the further device 602. The electronic system 100 can generate the connection setting by enabling or disabling a hardware component, a software component, or a combination thereof.

The preferred arrangement 610 is an optimal physical arrangement of the attachable device 302 and the further device 602 for performing a functional task related to the carrier 304. For example, the preferred arrangement can include a physical arrangement of the attachable device 302 and the further device 602 optimized for tracking a particular instance of the biometric indicator 514 of FIG. 5.

Figure 7:
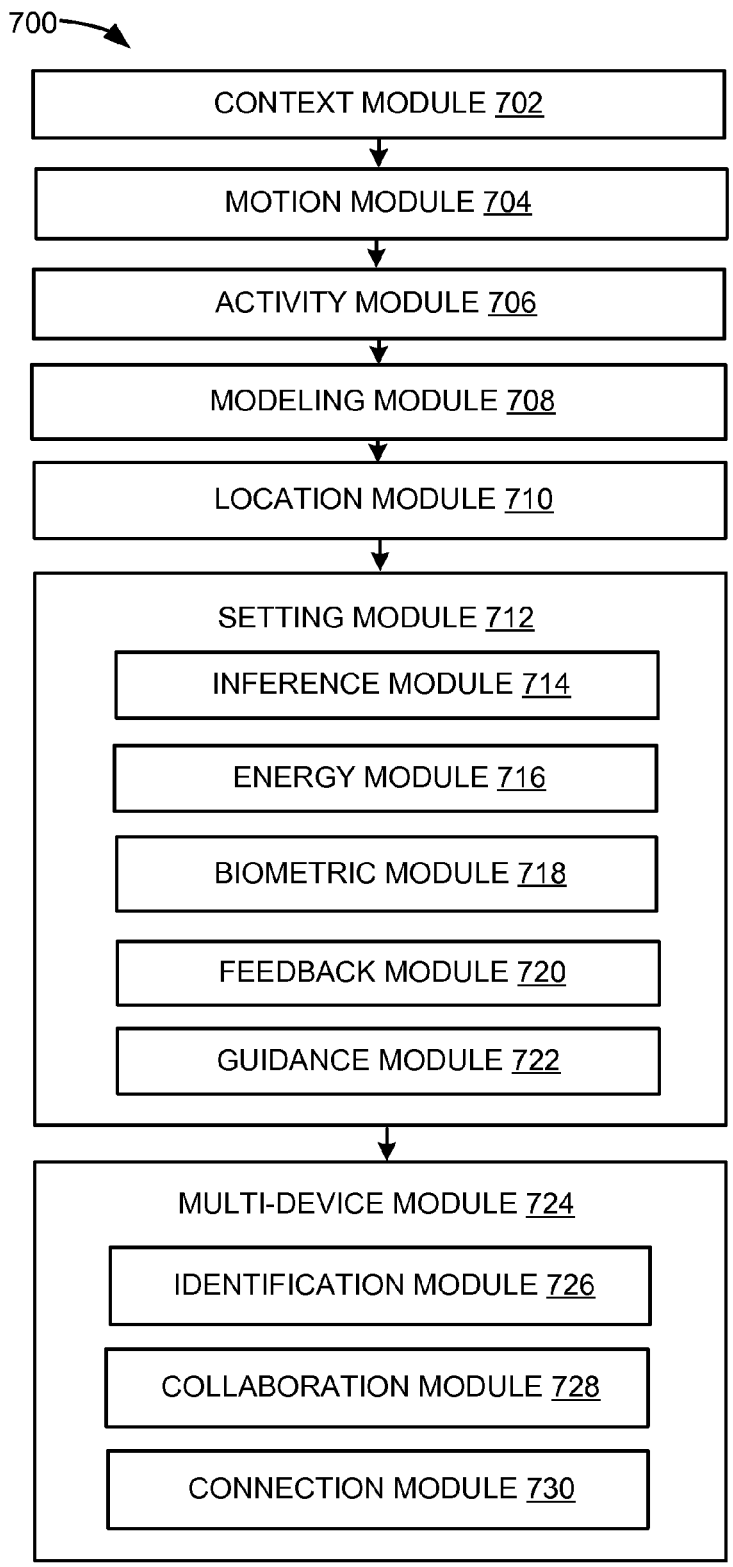
FIG. 7 is a control flow of the electronic system.

Referring now to FIG. 7, therein is shown a control flow 700 of the electronic system 100 of FIG. 1. The electronic system 100 can include a context module 702, a motion module 704, an activity module 706, a modeling module 708, a location module 710, a setting module 712, a multi-device module 724, or a combination thereof. The modules can be coupled by having the input of one module connected to the output of another, such as by using wired or wireless connections, the communication path 104 of FIG. 1, instructional steps, process sequence, or a combination thereof.

The modules can be coupled directly, without any intervening structures other than the structure providing the direct connection. The modules can also be coupled indirectly, through a shared connection or other functional structures between the coupled modules.

The context module 702 is configured to determine the usage context 508 of FIG. 5. The context module 702 can determine the usage context 508 based on a usage time, an environmental context, a usage location, or a combination thereof.

The context module 702 can determine the usage context 508 by determining the usage time. The usage time can include a time-of-day, a day-of-the-week, a specific calendar day, a usage period, or a combination thereof. The context module 702 can determine the usage time using the first control unit 212 of FIG. 2, the second control unit 234 of FIG. 2, or a combination thereof. In addition, the context module 702 can determine the usage time by accessing a calendar application, a time-keeping application, an itinerary application, or a combination thereof.

The context module 702 can also determine the usage context 508 by determining the environmental context. The environmental context can refer to an ambient light level, an ambient temperature, an ambient noise level, or a combination thereof. For example, the context module 702 can use one or more MEMS sensors housed in the attachable device 302 of FIG. 3 to detect the level of ambient light, the ambient temperature, or a combination thereof in the vicinity of the attachable device 302. Moreover, the context module 702 can use the audio unit 227 to detect the ambient noise level.

The context module 702 can also determine the usage context 508 by determining the usage location. The usage location can refer to a geographic location of the carrier 304 of FIG. 3 when the motion 320 of FIG. 3 is detected. The context module 702 can use the location unit 220 to determine the usage location. The context module 702 can further classify the usage location with a location identifier such as "work," "home," or "gym" by accessing a database or application containing map information, address information, or a combination thereof.

The context module 702 can also determine the usage context 508 by determining the carrier type 306 of FIG. 3. The context module 702 can determine the carrier type 306 based on the contact reading 312 of FIG. 3 obtained through the attachable device 302 when the attachable device 302 is attached to the carrier 304. The contact reading 312 can involve a skin impedance, a surface impedance, a skin resistance, a surface resistance, a skin conductance, a surface conductance, or a combination thereof.

The context module 702 can use one or more instances of the electric potential sensor 223 of FIG. 2 or any other electrical sensors to obtain the contact reading 312. The context module 702 can use differences in the impedance, resistance, or conductance measurements to distinguish between multiple instances of the carrier type 306.

For example, the attachable device 302 can be attached to a body part of the carrier 304 representing the human user 308 of FIG. 3 such as an arm or torso. The context module 702 can determine the carrier type 306 as the human user 308 based on the contact reading 312 representing a conductance measurement, an impedance measurement, or a combination thereof for human skin. As a more specific example, the context module 702 can distinguish between the human user 308 and the object 310 of FIG. 3 based on differences in the electrical properties of biological surfaces and non-biological surfaces.

The context module 702 can store information concerning the usage context 508 in the first storage unit 214 of FIG. 2, the second storage unit 246 of FIG. 2, or a combination thereof. The context module 702 can be part of the first software 226 of FIG. 2, the second software 242 of FIG. 2, or a combination thereof. The first control unit 212 of FIG. 2 can execute the first software 226, the second control unit 234 of FIG. 2 can execute the second software 242, or a combination thereof to determine the usage context 508.

Moreover, the context module 702 can also communicate the usage context 508 between devices through the first communication unit 216 of FIG. 2, the second communication unit 236 of FIG. 2, or a combination thereof. After determining the usage context 508, the control flow 700 can pass from the context module 702 to the motion module 704.

The motion module 704 is configured to capture the motion profile 322 of FIG. 3. The motion profile 322 can include motion data and geospatial data concerning the motion 320. The motion 320 can be associated with a movement of a portion of the carrier 304 such as a body part or door. The motion 320 can be made by the carrier 304 while the carrier 304 undertakes a geographical displacement relative to a coordinate or a geographical location. Alternatively, the motion 320 can be made by the carrier 304 while the carrier 304 remains in place.

For example, the motion 320 can include a hip extension motion undertaken in the course of an ambulatory instance of the activity 502 such as walking, jogging, or jumping. As an additional example, the motion 320 can include a plantar flexion motion undertaken during a stationary instance of the activity 502 such as standing, sitting, or sleeping. The activity 502 will be discussed in more detail in the sections below.

The motion module 704 can capture the motion profile 322 by using the attachable device 302 to obtain information concerning the displacement change 402 of FIG. 4, the orientation change 408 of FIG. 4, the device movement 506 of FIG. 4, or a combination thereof. The motion module 704 can capture the motion profile 322 by collecting or sampling coordinates, geographic positions, proximity signals, orientation angles, or a combination thereof of the attachable device 302.

For example, the motion module 704 can capture the motion profile 322 by using the location unit 220 of FIG. 2, the first communication unit 216 of FIG. 2, or a combination thereof to obtain information concerning the device movement 506. As a more specific example, the activity module 706 can use the GPS component of the location unit 220, the first communication unit 216, or a combination thereof to obtain coordinate information, geographic information, proximity information, or a combination thereof pertaining to the device movement 506. Moreover, the activity module 706 can use the accelerometer component of the inertial measurement unit 221 of FIG. 2 to obtain acceleration information pertaining to the device movement 506.

As an additional example, the motion module 704 can capture the motion profile 322 by determining one or more instances of the measured spatial position 404 of FIG. 4. The motion module 704 can use the inertial measurement unit 221, the electric potential sensor 223, or a combination thereof to determine the measured spatial position 404.

Also, for example, the motion module 704 can determine the measured spatial position 404 relative to a position of the carrier 304. As a more specific example, the motion module 704 can use the electric potential sensor 223 to determine the measured spatial position 404 relative to a segment of the human user 308 or the object 310. As an additional example, the motion module 704 can determine the measured spatial position 404 relative to a position of a stationary object or person.

The motion module 704 can also use the electric potential sensor 223 to detect the displacement change 402 based on the measured spatial position 404. For example, the motion module 704 can detect the displacement change 402 based on an initial instance of the measured spatial position 404 and a subsequent instance of the measured spatial position 404.

In addition, the motion module 704 can use the gyroscope component of the inertial measurement unit 221 to detect the orientation change 408. As a more specific example, the motion module 704 can detect the orientation change 408 as a change in a rotation angle of the attachable device 302 such as a change in yaw, pitch, roll, or a combination thereof.

The motion module 704 can also capture the motion profile 322 based on the carrier type 306. For example, the motion module 704 can capture the motion profile 322 based on the carrier type 306 by adjusting the detection period 416 of FIG. 4 based on the carrier type 306. As a more specific example, the detection period 416 can be decreased when the carrier type 306 is the object 310 and increased when the carrier type 306 is the human user 308. As an even more specific example, the detection period 416 can range from several seconds to several hours or days.

The motion module 704 can capture the motion profile 322 based on the carrier type 306 by adjusting the number of data points sampled based on the carrier type 306. For example, the motion module 704 can bypass obtaining data concerning the orientation change 408 when the motion 320 of the carrier 304 does not allow for a change in the orientation of the attachable device 302.

Moreover, the motion module 704 can adjust the sensitivity of the electrical potential sensor 223, the response unit 225, the audio unit 227, or a combination thereof based on the carrier type 306. For example, the motion module 704 can increase or decrease a gain of an amplifier of the electrical potential sensor 223, the response unit 225, or a combination thereof based on the carrier type 306.

The motion module 704 can also include an indication of the motion profile 322 for representing a pattern, a periodicity, or a combination thereof concerning repeated instances of the motion 320, a frequency associated thereto, or a combination thereof. The motion module 704 can determine the motion 320 as repeating when the motion profile 322 includes duplicate or similar instances of the orientation data or movement data.

The motion module 704 can store the motion profile 322 in the first storage unit 214, the second storage unit 246, or a combination thereof. The motion module 704 can be part of the first software 226, the second software 242, or a combination thereof. The first control unit 212 can execute the first software 226, the second control unit 234 can execute the second software 242, or a combination thereof to capture the motion profile 322.

Moreover, the motion module 704 can also communicate the motion profile 322 between devices through the first communication unit 216, the second communication unit 236, or a combination thereof. After generating the motion profile 322, the control flow 700 can pass from the motion module 704 to the activity module 706.

The activity module 706 is configured to determine the activity 502 of FIG. 5. The activity module 706 can determine the activity 502 based on the motion profile 322, the carrier type 306, the usage context 508, the training profile 512 of FIG. 5, or a combination thereof.

The activity module 706 can determine a subset of the training profile 512 by filtering or narrowing down the training profile 512 based on the carrier type 306, the usage context 508, or a combination thereof. For example, the context module 702 can determine the carrier type 306 as the human user 308 or the object 310, and the activity module 706 can filter for instances of the training profile 512 corresponding to either the object 310 or the human user 308. As an additional example, the context module 702 can filter for instances of the training profile 512 corresponding to or matching the usage context 508, such as the usage time, the usage location, a usage category, or a combination thereof.

The activity module 706 can then determine the activity 502 by comparing the motion profile 322 with the subset of the training profile 512. The activity module 706 can compare the motion profile 322 with the subset of the training profile 512 by applying a classification algorithm or technique. For example, the activity module 706 can determine the activity 502 by applying a naïve Bayesian classifier, a probabilistic classifier, a pattern recognition technique, or a combination thereof to classify the motion profile 322 with an instance of the training profile 512 associated with a known instance of the activity 502.

For example, the context module 702 can determine the carrier type 306 as the human user 308 and the motion profile 322 can include GPS data of the attachable device 302 moving between five to six miles per hour and accelerometer data depicting intermittent horizontal accelerations and vertical accelerations. The activity module 706 can first filter for instances of the training profile 512 corresponding to the human user 308. The activity module 706 can then compare the motion profile 322 with the subset of the training profile 512 and determine the activity 502 as a running or jogging activity.

As an additional example, the motion profile 322 of the human user 308 can include GPS data showing the human user 308 has not moved within a threshold period initially predetermined by the electronic system 100. In addition, the motion profile 322 can include gyroscope data showing small orientation changes. Based on this information, the activity module 706 can determine the activity 502 as a sedentary activity such as sleeping, sitting, or working at a desk.

The activity module 706 can be part of the first software 226, the second software 242, or a combination thereof. The first control unit 212 can execute the first software 226, the second control unit 234 can execute the second software 242, or a combination thereof to determine the activity 502.

Moreover, the activity module 706 can also communicate the activity 502 between devices through the first communication unit 216, the second communication unit 236, or a combination thereof. After determining the activity 502, the control flow 700 can pass from the activity module 706 to the modeling module 708.

The modeling module 708 is configured to determine the kinematic model 324 of FIG. 3 for representing the motion 320 of the carrier 304. The kinematic model 324 can include one or more kinematic equations, kinematic matrices such as a multi-dimensional matrix or a Jacobian matrix, kinematic constraint equations, or a combination thereof.

The electronic system 100 can generate or update the kinematic model 324, obtain the kinematic model 324 from an external database or storage medium, or a combination thereof. The electronic system 100 can store instances of the kinematic model 324 in the first storage unit 214, the second storage unit 246, or a combination thereof. The modeling module 708 can use the first storage interface 224 of FIG. 2, the second storage interface 248 of FIG. 2, or a combination thereof to access one or more instances of the kinematic model 324.

The modeling module 708 can determine the kinematic model 324 in a number of ways. For example, the modeling module 708 can determine the kinematic model 324 based on the carrier type 306, the usage context 508, the activity 502, the motion profile 322, or a combination thereof.

The modeling module 708 can determine the kinematic model 324 by filtering instances of the kinematic model 324 based on the carrier type 306. For example, the context module 702 can determine the carrier 304 as the human user 308. The modeling module 708 can then filter for instances of the kinematic model 324 corresponding to the human user 308. As an additional example, the context module 702 can identify the carrier 304 as an appliance representing the object 310. In this example, the modeling module 708 can then filter for instances of the kinematic model 324 associated with the appliance.

The modeling module 708 can also determine the kinematic model 324 based on the activity 502. For example, the activity module 706 can determine the activity 502 as a slow-paced walk, the modeling module 708 can then filter for instances of the kinematic model 324 appropriate for walking. As an additional example, the motion module 704 can determine the activity 502 as a sedentary activity such as sitting on a raised surface. In this example, the modeling module 708 can filter for instances of the kinematic model 324 appropriate for sitting.

The kinematic model 324 can include the joint-specific equation 326 of FIG. 3. Once the modeling module 708 has determined the kinematic model 324 based on the carrier type 306, the activity 502, or a combination thereof, the modeling module 708 can determine the joint-specific equation 326 appropriate for the motion 320 based on the motion profile 322. The modeling module 708 can determine the joint-specific equation 326 based on motion data or position data including the displacement change 402, the orientation change 408, or a combination thereof.

The modeling module 708 can determine the joint-specific equation 326 based on the displacement change 402 by comparing the displacement change 402 caused by the motion 320 against the distance constraints 410 of FIG. 4. More specifically, as an example, the modeling module 708 can compare the displacement change 402 of the attachable device 302 within a particular instance of the detection period 416 against the distance constraints 410 within the same instance of the detection period 416. The distance constraints 410 can represent a maximum instance of the displacement change 402 for a particular part of the carrier 304 including the joint 316 or multiple instances of the joint 316.

The modeling module 708 can also determine the joint-specific equation 326 based on the orientation change 408 by comparing the orientation change 408 caused by the motion 320 against the angular constraints 412 of FIG. 4. More specifically, as an example, the modeling module 708 can compare the orientation change 408 of the attachable device 302 within a particular instance of the detection period 416 against the angular constraints 412 within the same instance of the detection period 416.

The angular constraints 412 can represent a maximum instance of the orientation change 408 for a particular part of the carrier 304 including the joint 316 or multiple instances of the joint 316. The angular constraints 412 can also be represented as one or more angular degrees-of-freedom of the joint 316 or multiple instances of the joint 316.

For example, the modeling module 708 can detect the attachable device 302 as experiencing the orientation change 408 of 170 degrees of pitch and −40 degrees of yaw and the displacement change 402 of over 1 meter relative to a non-moving part of the carrier 304 based on the motion profile 322. In this example, the modeling module 708 can filter out or exclude certain instances of the kinematic model 324 and the joint-specific equation 326 based on the orientation change 408 and the displacement change 402.

As a more specific example, the modeling module 708 can filter out the joint-specific equation 326 for body parts or object parts unable to undertake such ranges of motion. Based on the example above, the modeling module 708 would rule out or exclude any instances of the kinematic model 324 or the joint-specific equation 326 related to the head, hands, or feet of the human user 308. As an additional example, the modeling module 708 can rule out the kinematic model 324 for the object 310 if the moving parts of the object 310 cannot cause the attachable device 302 to experience more than one instance of the orientation change 408 including a change in yaw and a change in pitch.

The distance constraints 410, the angular constraints 412, or a combination thereof can be initially predetermined by the electronic system 100. The modeling module 708 can adjust or build on predetermined instances of the distance constraints 410, the angular constraints 412, or a combination thereof through machine learning techniques, classifier training, or a combination thereof.

The electronic system 100 can obtain the distance constraints 410, the angular constraints 412, or a combination thereof from an external database or storage medium. In addition, the electronic system 100 can obtain the distance constraints 410, the angular constraints 412, or a combination thereof from a user of the electronic system 100 through a user input.

The distance constraints 410, the angular constraints 412, or a combination thereof can be stored in the first storage unit 214, the second storage unit 246, or a combination thereof. The distance constraints 410, the angular constraints 412, or a combination thereof can be associated with an individual instance of the joint 316 of FIG. 3, multiple instances of the joint 316, a body segment or object segment such as an upper body or lower body, or a combination thereof.

The modeling module 708 can be part of the first software 226, the second software 242, or a combination thereof. The first control unit 212 can execute the first software 226, the second control unit 234 can execute the second software 242, or a combination thereof to determine the kinematic model 324.

Moreover, the modeling module 708 can also communicate the kinematic model 324 between devices through the first communication unit 216, the second communication unit 236, or a combination thereof. After determining the kinematic model 324, the control flow 700 can pass from the modeling module 708 to the location module 710.

The location module 710 is configured to determine the attachment location 314 of FIG. 3 of the attachable device 302. The location module 710 can determine the attachment location 314 in a number of ways.

For example, the location module 710 can determine the attachment location 314 based on the motion profile 322, the kinematic model 324, the inverse kinematic solver of FIG. 4, or a combination thereof. More specifically, as an example, the location module 710 can determine the attachment location 314 by narrowing down the possible instances of the attachment location 314 to the joint segment 318 of FIG. 3. As previously discussed, the joint segment 318 can include a human limb, a part of a human limb, or a moveable component of the object 310.

The location module 710 can narrow down the attachment location 314 to the joint segment 318 by determining the joint 316 of FIG. 3 articulating the joint segment 318. The location module 710 can determine the joint 316 articulating the joint segment 318 by approximating the motion 320 of the carrier 304.

More specifically, as an example, the location module 710 can determine the joint 316 articulating the joint segment 318 by approximating the motion 320 of the carrier 304. As previously discussed, the motion 320 of the carrier 304 can be represented by motion data captured as part of the motion profile 322 such as the orientation change 408, the displacement change 402, the measured spatial position 404, or a combination thereof.

The location module 710 can determine the attachment location 314 based on the closed form solution 420 of FIG. 4. For example, the location module 710 can determine the attachment location 314 based on the closed form solution 420 by determining an expression or set of operations that can mimic the motion 320 of the joint segment 318.

The location module 710 can use an instance of the inverse kinematic solver 418 to approximate the motion 320 of the carrier 304. When applied to kinematics, the inverse kinematic solver 418 can approximate the motion 320 of the carrier 304 by comparing the modeled spatial position 406 of FIG. 4 with the measured spatial position 404 of the attachable device 302 resulting from the motion 320.

As a more specific example, the location module 710 can approximate the motion 320 by minimizing the difference between the modeled spatial position 406 and the measured spatial position 404. Minimizing the difference between the modeled spatial position 406 and the measured spatial position 404 will be discussed in more detail in the sections below.

The location module 710 can undertake the inverse kinematic solver 418 by iteratively applying the motion data from the motion profile 322 to different instances of the joint-specific equation 326. For example, the location module 710 can iteratively apply the motion data from the motion profile 322 to kinematic equations associated with a shoulder joint, a knee joint, an elbow joint, a hip joint, a torso joint, a hand joint, or any combination thereof. By doing so, the location module 710 can obtain multiple instances of the modeled spatial position 406 to compare against the measured spatial position 404.

As a more specific example, the location module 710 can apply motion data from the motion profile 322 to Equation (1) below representing an instance of the joint-specific equation 326 with an "n" number of joints. In this equation, "P" represents the modeled spatial position 406 at time "t", "$\theta_1 \ldots \theta_n$" represents multiple instances of the orientation change 408 captured by the motion profile 322, "j" represents all joints being articulated, "$L_1 \ldots L_n$" represents lengths of joint segments, and "K" represents constraints placed on the multi joint system including the angular constraints 412, the distance constraints 410, or a combination thereof:

$$P_n(t,j)=(L_1*\cos(\theta_1)(t)+L_2*\cos(\theta_1+\theta_2)(t)+L_n*\cos(\theta_1+\theta_2\ldots\theta_n(t))*K(j) \quad \text{Equation (1):}$$

The joint-specific equation 326 above can be modified as Equation (2) below to serve as the joint-specific equation 326 for a two jointed system such as an arm having an elbow joint and a shoulder joint:

$$P_2(t,j)=(L_1*\cos(\theta_1)(t)+L_2*\cos(\theta_1+\theta_2)(t))*K(j) \quad \text{Equation (2):}$$

For example, the attachable device 302 can be worn on a right wrist of the human user 308. In this example, the motion 320 can be a right elbow flexion motion involving an elbow joint. The location module 710 can approximate the motion 320 as the right elbow flexion motion by iteratively applying motion data from the motion profile 322 to all instances of the joint-specific equation 326 included as part of the kinematic model 324 identified by the motion module 704.

In doing so, the location module 710 can calculate numerous instances of the modeled spatial position 406. The location module 710 can then compare each calculated instance of the modeled spatial position 406 with the measured spatial position obtained from the motion profile 322.

The location module 710 can approximate the motion 320 by choosing the joint-specific equation 326 which minimizes the difference between the modeled spatial position 406 and the measured spatial position 404. In the example above, the location module 710 can determine the motion 320 as the right elbow flexion motion if the joint-specific equation 326 corresponding to the right elbow flexion motion produces the modeled spatial position 406 closest to the measured spatial position 404.

As a more specific example, the location module 710 can apply the error minimization function presented as Equation (3) below to the position results where "$P_{model}$" represents the modeled spatial position 406, "$P_{measured}$" represents the measured spatial position 404, "j" represents all joints being articulated, and "$\theta$" represents all orientation changes.

$$\text{Error}_{min}\forall j(\theta):F(j)=\Sigma_1{}^n P_{model}(t_n,j)-P_{measured}(t_n,j) \quad \text{Equation (3):}$$

Once the location module 710 has approximated the motion 320, the location module 710 can then associate the motion 320 with an instance of the joint 316 responsible for the motion 320. For example, once the location module 710 has approximated the motion 320 as the right elbow flexion motion, the location module 710 can associate the right elbow flexion motion with the right elbow joint.

The location module 710 can determine the attachment location 314 as the joint segment 318 articulated by the joint 316. In the case of the right elbow flexion motion, the location module 710 can determine the attachment location 314 as the right forearm of the human user 308.

In cases where multiple joints are responsible for the motion 320, the location module 710 can first narrow down the joint segment 318 to the two or more instances of the joint segment 318 included as part of the multi joint system. The location module 710 can then apply the motion data to only those instances of the joint-specific equation 326 relating to the multiple joints in the multi-joint system to determine the appropriate instance of the joint segment 318.

For example, the attachable device 302 can be worn on the right wrist of the human user 308 and the motion 320 can be a right arm motion involving both the shoulder joint and the elbow joint. Once the location module 710 has determined the right arm motion to be the motion 320, the location module 710 can then apply the motion data captured as part of the motion profile 322 to only instances of the joint-specific equation 326 associated with the shoulder joint and the elbow joint to narrow down the attachment location 314 to either the right forearm or the right bicep.

It has been discovered that determining the attachment location 314 using the inverse kinematic solver 418 provides a more efficient method of determining the attachment location 314. As an example, determining the attachment location 314 by choosing the joint-specific equation 326 which minimizes the difference between the modeled spatial position 406 and the measured spatial position 404 allows the electronic system 100 to quickly narrow down candidate instances of the joint 316 to those capable of producing the displacement change 402 and orientation change 408 detected by the attachable device 302.

The location module 710 can be part of the first software 226, the second software 242, or a combination thereof. The first control unit 212 can execute the first software 226, the second control unit 234 can execute the second software 242, or a combination thereof to determine the attachment location 314.

Moreover, the location module 710 can also communicate the attachment location 314 between devices through the first communication unit 216, the second communication unit 236, or a combination thereof. After determining the attachment location 314, the control flow 700 can pass from the location module 710 to the setting module 712.

The setting module 712 is configured to dynamically generate the device setting 504 of FIG. 5. Dynamically generating the device setting 504 can refer to the setting module 712 generating a new instance of the device setting 504 based on the attachment location 314 of the attachable device 302.

The setting module 712 can include an inference module 714, an energy module 716, a biometric module 718, a feedback module 720, a guidance module 722, or a combination thereof. The setting module 712 can dynamically generate the device setting 504 by generating the energy saving setting of FIG. 5, identifying and tracking the biometric indicator 514 of FIG. 5, generating the adjustable feedback 328 of FIG. 3, generating the positioning feedback 336 of FIG. 3, or a combination thereof based on the attachment location 314.

The inference module 714 is configured to determine the inferred usage 516 of FIG. 5. The inferred usage 516 can refer to a possible usage of the attachable device 302 determined by the electronic system 100. For example, the attachable device 302 can be used as the headset 520 of FIG. 5, the heart rate monitor 522 of FIG. 5, the activity tracker 524 of FIG. 5, the electromyography detector 526 of FIG. 5, the electrodermal activity detector 528 of FIG. 5, or a combination thereof.

The inference module 714 can determine the inferred usage 516 based on the attachment location 314, the usage context 508, and the usage profile 518 of FIG. 5. The usage profile 518 can include data or information pertaining to predetermined instances of the attachment location 314 corresponding to possible usages of the attachable device 302.

For example, the usage profile 518 for the headset 520 can correspond to the attachment location 314 of the attachable device 302 near an ear of the human user 308. As an additional example, the usage profile 518 for the heart rate monitor 522 can correspond to the attachment location 314 near the chest of the human user 308.

The usage profile 518 can also include data or information pertaining to the usage context 508 corresponding to a usage scenario. The usage profile 518 can initially be predetermined by the electronic system 100, generated based on historical usage patterns, or a combination thereof. The inference module 714 can determine the inferred usage 516 by comparing the attachment location 314 determined by the location module 710 with a stored instance of the attachment location 314 included as part of the usage profile 518.

The inference module 714 can determine the inferred usage 516 by comparing the attachment location 314 using a classification algorithm or technique. For example, the location module 710 can determine the attachment location 314 as an ear of the human user 308. In addition, the context module 702 can detect a sound coming from the mouth of the human user 308. In this example, the inference module 714 can determine the inferred usage 516 as the headset 520 based on the attachment location 314 of the ear and the sound coming from the human user 308.

The energy module 716 is configured to generate the energy saving setting 510. The energy module 716 can generate the energy saving setting 510 in a number of ways. The energy module 716 can generate the energy saving setting 510 by enabling or disabling a hardware component, a software component, a portion therein, or a combination thereof.

The energy module 716 can enable the hardware component by activating the hardware component, putting the hardware component in a wake mode, actively seeking a signal or ping from the hardware component, or a combination thereof. The energy module 716 can disable the hardware component by deactivating the hardware component, putting the hardware component in a sleep mode, ignoring a signal or ping from the hardware component, or a combination thereof. For example, the hardware component can include the first user interface 218, the first communication unit 216, the location unit 220, or a combination thereof.

The energy module 716 can enable the software component by calling a function from the software component, running a script from the software component, executing one or more portions of the software component, or a combination thereof. The energy module 716 can disable the software component by overriding a function call from the software component, not running a script from the software component, not executing a command from one or more portions of the software component, or a combination thereof. For example, the software component can include the first software 226.

The energy module 716 can generate the energy saving setting 510 based on the carrier type 306, the attachment location 314, the usage context 508, the motion profile 322, or a combination thereof. For example, the electronic system 100 can determine the carrier 304 as the object 310. The object 310 can include an appliance, a fixture, or a combination thereof. In this example, the energy module 716 can determine an instance of the energy saving setting 510 appropriate for the object 310.

As a more specific example, the attachable device 302 can be attached to the object 310 and the energy module 716 can enable the first control unit 212, the first communication unit 216, the first storage unit 214, and the inertial measurement unit 221 on the attachable device 302 for tracking movements, environmental factors, or a combination thereof associated with the object 310. More specifically, as an example, the attachable device 302 can be used to track the number of times a cover or door of the object 310 is opened.

In situations where the electronic system 100 determines the carrier type 306 as the human user 308, the energy module 716 can generate the energy saving setting 510 based on a position of the joint segment 318 associated with the attachment location 314 relative to a sensory organ of the human user 308. For example, the energy module 716 can generate the energy saving setting 510 based on a perceptibility of a hardware component by the sensory organ of the human user 308 as indicated by a model or structure of a human body.

The perceptibility of the hardware component can be determined based on known information concerning sight ranges and hearing ranges. For example, the energy module 716 can generate the energy saving setting based on a distance between the attachable device 302 and the eyes of the human user 308. In addition, the perceptibility of the hardware component can also be determined based on the usage context 508 including the level of ambient light or ambient noise.

The energy module 716 can also generate the energy saving setting 510 based on the inferred usage 516. For example, the location module 710 can determine the attachment location 314 as the ear of the human user 308 and the context module 702 can detect a sound coming from the mouth of the human user 308. In this example, the inference module 714 can determine the inferred usage 516 as the headset 520. The energy module 716 can generate the energy saving setting 510 by provisioning the attachable device 302 as the headset 520.

The energy module 716 can provision the attachable device 302 as the headset 520 by enabling both the first communication unit 216 and the audio unit 227. Additionally, the energy module 716 can generate the energy saving setting 510 by disabling the first display interface 230, the response unit 225, the electrical potential sensor 223, the GPS component of the location unit 220, or a combination thereof. Moreover, the energy module 716 can generate the energy saving setting 510 by disabling one or more software components associated with such hardware components.

The energy module 716 can also generate the energy saving setting 510 based on the inferred usage 516 and the activity 502. For example, the location module 710 can determine the attachment location 314 as the chest of the human user 308 and the context module 702 can detect the usage context 508 as an outdoor environment. Moreover, the activity module 706 can detect the activity 502 as a jog based on the motion profile 322. In this example, the inference module 714 can determine the inferred usage 516 as the heart rate monitor 522. The energy module 716 can generate the energy saving setting 510 by provisioning the attachable device 302 as the heart rate monitor 522.

The energy module 716 can provision the attachable device 302 as the heart rate monitor 522 by enabling the electrical potential sensor 223, the audio unit 227, the location unit 220, the response unit 225, or a combination thereof. Additionally, the energy module 716 can generate the energy saving setting 510 by disabling the first communication unit 216, the first display interface 230, or a combination thereof. Moreover, the energy module 716 can generate the energy saving setting 510 by disabling one or more software components associated with such hardware components.

As an additional example, the location module 710 can determine the attachment location 314 as the hip of the human user 308, the context module 702 can determine the usage context 508 as an outdoor environment, and the activity module 706 can detect the activity 502 as a walk. In this example, the inference module 714 can determine the inferred usage 516 as the activity tracker 524. The energy module 716 can generate the energy saving setting 510 by provisioning the attachable device 302 as the activity tracker 524.

The energy module 716 can provision the attachable device 302 as the activity tracker 524 by enabling the location unit 220 and disabling the first display interface 230, the electrical potential sensor 223, the audio unit 227, the response unit 225, or a combination thereof. Moreover, the energy module 716 can generate the energy saving setting 510 by disabling one or more software components associated with such hardware components.

The energy module 716 can also generate the energy saving setting 510 by adjusting a switching frequency of one or more hardware components of the attachable device 302 including the location unit 221, the first communication unit 216, or a combination thereof. In addition, the energy module 716 can generate the energy saving setting 510 by decreasing a sensitivity of a hardware component such as the response unit 225, the audio unit 229, or a combination thereof.

It has been discovered that generating the energy saving setting 510 based on the attachment location 314 provides for improved resource usage. As an example, generating the energy saving setting 510 by enabling or disabling select hardware components and software components ensures that energy is not being wasted on keeping unused or inaccessible components of the attachable device 302 active.

The biometric module 718 is configured to dynamically identify the biometric indicator 514 based on the attachment location 314, the usage context 508, the motion profile 322, or a combination thereof. In addition, the biometric module 718 is configured to track the biometric indicator 514 at the attachable device 302.

The biometric module 718 can dynamically identify the biometric indicator 514 based on the attachment location 314 by referencing the anatomical model 414 of FIG. 4. The anatomical model 414 can be a model describing the anatomy of the carrier 304. For example, when the carrier type 306 is the human user 308, the biometric module 718 can refer to the anatomical model 414 of a human body.

The biometric module 718 can use the anatomical model 414 to determine an accessibility of the biometric indicator 514 to the attachable device 302 at the attachment location 314. For example, the biometric module 718 can use the anatomical model 414 to determine whether a heartbeat can be measured when the attachment location 314 of the attachable device 302 is more than a threshold distance from the heart. Moreover, the biometric module 718 can use the anatomical model 414 to determine all instances of the biometric indicator 514 which can be measured from the attachment location 314.

The biometric module 718 can dynamically identify the biometric indicator 514 based on an accuracy of measurement from the attachment location 314. The accuracy measurement can be determined by comparing the biometric indicator 514 obtained by the attachable device 302 with an average or median value initially predetermined by the electronic system 100.

In addition, the biometric module 718 can dynamically identify the biometric indicator 514 based on the usage profile 518. For example, the usage profile 518 can associate the attachment location 314 representing a part of the carrier 304 with a particular instance of the biometric indicator 514.

As a more specific example, the usage profile 518 can associate the attachment location 314 representing a forearm of the human user 308 with the biometric indicator 514 of surface electromyography signals. As an additional example, the usage profile 518 can associate the attachment location 314 representing a hand of the human user 308 with the biometric indicator 514 of electrodermal activity.

The usage profile 518 associating the attachment location 314 with the biometric indicator 514 can be initially predetermined by the electronic system 100. In addition, the biometric module 718 can update the usage profile 518 based on the accuracy of such measurements.

The biometric module 718 can track the biometric indicator 514 for a limited duration or an extended duration. The biometric module 718 can track the biometric indicator 514 by collecting or sampling signal data, audio data, or a combination thereof concerning one or more organs, muscles, or joints of the carrier 304. The biometric module 718 can also track the biometric indicator 514 by enabling or disabling certain hardware components, software components, or a combination thereof.

In addition, the biometric module 718 can track the biometric indicator 514 by taking advantage of different functionalities of the same hardware component. For example, the biometric module 718 can use the electrical potential sensor 223 to measure both a surface electromyography signal and an electrodermal activity.

For example, the biometric module 718 can determine the attachment location 314 as the forearm of the human user 308. In addition, the context module 702 can determine the usage context 508 as an indoor environment and the motion module 704 can detect the activity 502 as exhibiting little geographic movement. In this example, the biometric module 718 can identify the biometric indicator 514 to be tracked as an electromyography signal and provision the attachable device 302 as the electromyography detector 526.

As an additional example, the location module 710 can determine the attachment location 314 as the hand of the human user 308. In addition, the context module 702 can determine the usage time as a work day and the usage location as a workplace of the human user 308. In this example, the biometric module 718 can identify the biometric indicator 514 to be tracked as an electrodermal activity signal. The biometric module 718 can enable the same instance of the electrical potential sensor 223 used to track the electromyography signal to track the electrodermal activity signal. In this case, the biometric module 718 can provision the attachable device 302 as the electrodermal activity detector 528.

The biometric module 718 can also generate the biometric marker 530 of FIG. 5 based on the attachment location 314. The biometric module 718 can generate the biometric marker 530 as an upper or lower signal threshold for the biometric indicator 514 detected at the attachment location 314. For example, the biometric marker 530 can be a heart rate above 160 beats per minute or an EEG signal with a frequency below 7 Hz. The signal thresholds representing the biometric marker 530 can be stored in the first storage unit 214, the second storage unit 246, or a combination thereof.

The biometric marker 530 can be implemented as an electronic marker, flag, interrupt, or a combination thereof. The biometric module 718 can generate an alert or notification when an instance of the biometric indicator 514 reaches a level indicated by the biometric marker 530.

It has been discovered that dynamically identifying the biometric indicator 514 based on the attachment location 314 enhances the fungibility of the attachable device 302. As an example, dynamically generating an instance of the device setting 504 for tracking the biometric indicator 514 most accessible to the attachable device 302 at the attachment location 314 allows the same device to be used for multiple purposes and reduces the need for a user to manually re-configure the device each time.

The feedback module 720 is configured to generate the adjustable feedback 328. The feedback module 720 can generate the adjustable feedback 328 at the attachable device 302. In addition, the feedback module 720 can generate the adjustable feedback 328 based on the attachment location 314.

The adjustable feedback 328 can include the haptic feedback 330 of FIG. 3, the audio feedback 332 of FIG. 3, the visual feedback 334 of FIG. 3, or a combination thereof. More specifically, as an example, the haptic feedback 330 can include a vibrational stimulus generated by the attachable device 302. The feedback module 720 can use one or more components of the response unit 225 to generate the haptic feedback 330.

For example, one or more instances of the response unit 225 can be enclosed in the fastening unit 103 of the attachable device 302. The feedback module 720 can generate the haptic feedback 330 by using actuators to generate a vibrational response through the fastening unit 103. As an additional example, one or more instances of the response unit 225 can be coupled, directly or indirectly, to an underside of the first display interface 230 of the attachable device 302 and the feedback module 720 can generate the haptic feedback 330 directly at the attachable device 302.

The audio feedback 332 can include an acoustic signal generated by the attachable device 302. More specifically, as an example, the feedback module 720 can use the audio unit 227 to generate the audio feedback 332. For example, the audio feedback 332 can include a sound effect, a beeping sound, a ringtone, or a combination thereof.

The visual feedback 334 can include a light emission, a change in a display interface such as the first display interface 230, or a combination thereof. The feedback module 720 can use the first display interface 230 to generate the visual feedback 334. Alternatively, the feedback module 720 can use one or more LEDs embedded in the attachable device 302 to generate the visual feedback 334.

The feedback module 720 can generate the adjustable feedback 328 by enabling or disabling any of the haptic feedback 330, the audio feedback 332, the visual feedback 334, or a combination thereof based on the attachment location 314. In addition, the feedback module 720 can generate the adjustable feedback 328 by modulating or adjusting the strength, frequency, or duration of any of the haptic feedback 330, the audio feedback 332, the visual feedback 334, or a combination thereof based on the attachment location 314. Moreover, the feedback module 720 can module or adjust any combination of the strength, frequency, or duration of the adjustable feedback 328.

The feedback module 720 can modulate or adjust the strength, frequency, or duration of any of the haptic feedback 330, the audio feedback 332, the visual feedback 334, or a combination thereof based on a sensitivity of the joint segment 318 serving as the attachment location 314, a perceptibility of the feedback, or a combination thereof. For example, the feedback module 720 can increase the frequency, strength, or duration of the adjustable feedback 328 when the attachable device 302 is attached to an instance of the joint 316 or the joint segment 318 having less sensitive nerve endings such as a lower leg or ankle.

Alternatively, the feedback module 720 can decrease the frequency, strength, or duration of the adjustable feedback 328 when the attachable device 302 is attached to an instance of the joint 316 or the joint segment 318 having more sensitive nerve endings such as a forehead, neck, or upper chest. Moreover, the feedback module 720 can disable the audio feedback 332 when the attachable device 302 is attached further from the ear and enable the audio feedback 332 when the attachable device is attached closer to the ear.

Moreover, the feedback module 720 can fine tune the frequency, strength, or duration of the adjustable feedback 328 based on the usage context 508 and the attachment location 314. For example, the feedback module 720 can increase the strength of the adjustable feedback 328, such as the haptic feedback 330 or the visual feedback 334, when the electronic system 100 determines the usage context 508 is an outdoor environment. As an additional example, the feedback module 720 can decrease the strength of the adjustable feedback 328 such as the audio feedback 332 or the haptic feedback 330 when the electronic system 100 determines the usage context 508 as an indoor environment and the ambient noise level as low such as in a meeting room or elevator.

It has been discovered that generating the adjustable feedback 328 at the attachable device 302 based on the attachment location 314 improves the user's experience with the attachable device 302. As an example, generating the adjustable feedback 328 by adjusting the strength, frequency, or duration of any of the haptic feedback 330, the audio feedback 332, the visual feedback 334, or a combination thereof ensures that the carrier 304 is made aware of the adjustable feedback 328. Moreover, adjusting the strength, frequency, or duration of the adjustable feedback 328 reduces the possibility of the adjustable feedback 328 being viewed as intrusive.

The guidance module 722 is configured to generate the positioning feedback 336 for guiding the carrier 304 or a user of the electronic system 100 to move the attachable device 302 to a new instance of the attachment location 314. The guidance module 722 can guide the carrier 304 or the user by generating the positioning feedback 336 until the attachable device 302 is moved to the new instance of the attachment location 314.

The guidance module 722 can guide the carrier 304 or the user of the electronic system 100 attachable device 302 to the new instance of the attachment location 314 for improving a functionality of the attachable device 302. In addition, the guidance module 722 can guide the carrier 304 or the user of the electronic system 100 to a new instance of the attachment location 314 for improving a measurement of the biometric indicator 514.

The guidance module 722 can generate the positioning feedback 336 by generating the haptic feedback 330, the audio feedback 332, the visual feedback 334, or a combination thereof. The guidance module 722 can use one or more instances of the response unit 225, the audio unit 227, the first display interface 230, or a combination thereof to generate the positioning feedback 336.

The guidance module 722 can generate the positioning feedback 336 based on a current instance of the attachment location 314, the inferred usage 516, the usage context 508, the motion profile 322, or a combination thereof. For example, the location module 710 can determine a current instance of the attachment location 314 as an upper thigh of the human user 308. The context module 702 can also determine the usage context 508 as an outdoor environment and the activity module 706 can determine the activity 502 as a walk.

In this example, the inference module 714 can determine the inferred usage 516 of the attachable device 302 as the activity tracker 524. The guidance module 722 can generate the positioning feedback 336 to guide the attachable device 302 to a new instance of the attachment location 314 more appropriate for the activity tracker 524 based on the usage profile 518 such as a hip region or waist region.

As an additional example, the location module 710 can determine a current instance of the attachment location 314 as a forearm of the human user 308. The guidance module 722 can determine the inferred usage 516 as the electromyography detector 526 based on the attachment location 314. The guidance module 722 can generate the positioning feedback 336 to guide the carrier 304 or the user of the electronic system 100 to move the attachable device 302 to a more specific instance of the attachment location 314, such as the upper forearm region, for optimizing the functionality of the attachable device 302 as the electromyography detector 526.

The guidance module 722 can also generate the positioning feedback 336 based on the biometric indicator 514 tracked by the attachable device 302 and the attachment location 314. For example, the biometric module 718 can be tracking the heart rate of the human user 308. In addition, the activity module 706 can determine the activity 502 as a jog. Moreover, the location module 710 can determine the attachment location 314 as shifting away from the lower chest region over the detection period 416. For example, the attachment location 314 of the attachable device 302 can shift as a result of frictional forces or physical forces caused by the running motion.

Under these circumstances, the guidance module 722 can generate the positioning feedback 336 to guide the carrier 304 or the user of the electronic system 100 to move the attachable device 302 to a new instance of the attachment location 314 more suitable optimized for tracking the heart rate of the human user 308. The guidance module 722 can access information from the usage profile 518, the kinematic model 324, the anatomical model 414, or a combination thereof for determining the attachment location 314 optimized for tracking the heart rate of the human user 308.

It has been discovered that generating the positioning feedback 336 based on the attachment location 314 improves the accuracy of the attachable device 302 in providing health monitoring and tracking functions. As an example, generating the positioning feedback 336 to guide the carrier 304 or the user of the electronic system 100 to move the attachable device 302 to a more suitable instance of the attachment location 314 ensures the biometric indicator 514 is more accessible to the attachable device 302.

The setting module 712 can be part of the first software 226, the second software 242, or a combination thereof. The first control unit 212 can execute the first software 226, the second control unit 234 can execute the second software 242, or a combination thereof to dynamically generate the device setting 504.

Moreover, the location module 710 can also communicate the device setting 504 between devices through the first communication unit 216, the second communication unit 236, or a combination thereof. After generating the device setting 504, the control flow 700 can pass from the setting module 712 to the multi-device module 724.

The multi-device module 724 is configured to identify the further device 602 of FIG. 6 for interacting with the attachable device 302 and generate a connection setting 608 for communicating with the further device 602. The multi-device module 724 can include an identification module 726, a collaboration module 728, a connection module 730, or a combination thereof.

The modules can be coupled to one another and the control flow 700 can pass from one module to another module directly or indirectly. For example, the control flow 700 can pass from the identification module 726 to the connection module 730 directly or through the collaboration module 728.

The identification module 726 is configured to identify the further device 602 for interacting with the attachable device 302. The further device 602 can include another instance of the attachable device 302, the second device 106, or a combination thereof. For example, the attachable device 302 can be a watch-type device attached to a wrist of the human user 308 and the further device 602 can be another instance of the attachable device 302 attached to the thigh of the human user 308. As an additional example, the attachable device 302 can be the activity tracker 524 and the further device 602 can be a mobile phone carried by the human user 308.

The attachable device 302 can communicate with the further device 602 through the communication path 104. For example, the attachable device 302 can communicate with the further device 602 over a Bluetooth™ Low Energy connection, a radio frequency connection, a WiFi connection, or a combination thereof.

The identification module 726 can identify the further device 602 based on a geographic proximity to the further device 602, a communication signal received from the further device 602, or a combination thereof. For example, the identification module 726 can identify the further device 602 when the identification module 726 identifies a beacon signal transmitted by the further device 602. As an additional example, the identification module 726 can identify the further device 602 when the further device 602 is located within 10 meters of the attachable device 302.

In cases where the further device 602 is another instance of the attachable device 302, the identification module 726 can interact with the location module 710 to determine the attachment location 314 of the further device 602. Moreover, the identification module 726 can receive a user input concerning the attachment location 314 of the further device 602.

In cases where the further device 602 is not another instance of the attachable device 302, the identification module 726 can identify the further device 602 by determining a device type and a functional capability of the further device 602 based on a protocol or procedure predetermined by the electronic system 100. For example, the identification module 726 can identify the further device 602 as a smartphone or tablet device. As an additional example, the identification module 726 can identify the further device 602 as a WiFi-enabled video camera.

The collaboration module 728 is configured to determine the collaboration context 604 of FIG. 6. The collaboration module 728 can determine the collaboration context 604 based on the usage context 508, the collaboration arrangement 606 of FIG. 6, or a combination thereof. The collaboration module 728 can determine the collaboration context 604 in a number of ways.

The collaboration module 728 can determine the collaboration context 604 based on the usage context 508. More specifically, as an example, the collaboration module 728 can determine the usage context 508 including the usage time, the usage location, and the environmental context when the identification module 726 identifies the further device 602. For example, the collaboration module 728 can determine the collaboration context 604 as 3 pm on a Saturday in an outdoor environment.

The collaboration module 728 can also determine the collaboration context 604 based on the collaboration arrangement 606. The collaboration arrangement 606 can refer to a physical arrangement of the attachable device 302 and the further device 602 relative to the carrier 304. When the further device 602 is another instance of the attachable device 302, the collaboration module 728 can determine the collaboration arrangement 606 based on the attachment location 314 of the attachable device 302 and the further device 602. In cases where the further device 602 is not another instance of the attachable device 302, the collaboration module 728 can determine the location of the further device 602 based on an input from the further device 602, a user, or another device in the electronic system 100.

As a more specific example, the collaboration module 728 can determine the collaboration arrangement 606 as three instances of the attachable device 302 attached to a chest area of the human user 308. As an additional example, the collaboration module 728 can determine the collaboration arrangement 606 as the attachable device 302 attached to a wrist of the human user 308 and a smartphone located in a right front pocket of the human user 308.

The collaboration module 728 can store information concerning the collaboration context 604 in the first storage unit 214, the second storage unit 246, or a combination thereof. The collaboration module 728 can also access previous instances of the collaboration context 604 through the first storage interface 224 of FIG. 2, the second storage interface 248 of FIG. 2, or a combination thereof. The collaboration module 728 can access previous instances of the collaboration context 604 to compare the current instance of the collaboration context 604 with the previous instances of the collaboration context 604.

The connection module 730 is configured to generate the connection setting 608 of FIG. 6 for communicating with the further device 602. The connection module 730 can generate the connection setting 608 for improving or enhancing a functionality of the attachable device 302 based on the presence of the further device 602. The connection module 730 can generate the connection setting 608 based on the collaboration context 604, the collaboration arrangement 606, the preferred arrangement 610 of FIG. 6, the biometric marker 530, or a combination thereof.

The preferred arrangement 610 can represent a preferred or optimal physical arrangement of the attachable device 302 and the further device 602 for performing a functional task related to the carrier 304. For example, the preferred arrangement 610 can include a preferred or optimal physical arrangement of the attachable device 302 and the further device 602 for taking an EEG of the brain. As an additional example, the preferred arrangement 610 can include the preferred or optimal physical arrangement of three instances of the attachable device 302 for taking an ECG of the human user 308.

The connection module 730 can generate the connection setting 608 by generating the adjustable feedback 328, the positioning feedback 336, or a combination thereof. For example, the connection module 730 can generate a combination of the adjustable feedback 328 and the positioning feedback 336 to change the collaboration arrangement 606 into the preferred arrangement 610. The connection module 730 can also change the collaboration arrangement 606 into the preferred arrangement 610 by guiding the carrier 304 or the user of the electronic system 100 to move the attachable device 302, the further device 602, or a combination thereof into new instances of the attachment location 314 corresponding to the preferred arrangement 610.

For example, the collaboration module 728 can determine the collaboration arrangement 606 as three instances of the attachable device 302 located around a chest area of the human user 308. In this example, the connection module 730 can generate the connection setting 608 by generating a combination of the adjustable feedback 328 and the positioning feedback 336 to guide the carrier 304 or the user of the electronic system 100 to move one or more instances of the attachable device 302 into an alignment or physical arrangement corresponding to the preferred arrangement 610 for an ECG.

The connection module 730 can generate the connection setting 608 by enabling or disabling a hardware component, a software component, a portion therein, or a combination thereof. In addition, the connection module 730 can generate the connection setting 608 by overriding the energy saving setting 510.

In the example above involving the ECG monitor, the connection module 730 can generate the connection setting 608 by enabling the electrical potential sensor 223 and the first communication unit 216 of the three instances of the attachable device 302. Moreover, the connection module 730 can generate the connection setting 608 by disabling certain hardware units of three instances of the attachable device 302 including the first display interface 230, the response unit 225, and the audio unit 227.

As an additional example, the identification module 726 can identify a navigation device representing the further device 602. In addition, the collaboration module 728 can determine the collaboration context 604 as the navigation device actively routing the carrier 304 to a geographic location. Moreover, the collaboration module 728 can determine the collaboration arrangement 606 as a first instance of the attachable device 302 located on the right arm of the carrier 304 and a second instance of the attachable device 302 located on the left arm.

In this example, the connection module 730 can generate the connection setting 608 by selectively generating the adjustable feedback 328 based on the attachment location 314 for routing the carrier 304. More specifically, as an example, the connection module 730 can generate the haptic feedback 330 at the first instance of the attachable device 302 to suggest a rightward maneuver and generate the haptic feedback 330 at the second instance of the attachable device 302 to suggest a leftward maneuver.

The connection module 730 can also generate the connection setting 608 based on the biometric marker 530. For example, the attachable device 302 can be attached to a hand of the human user 308 and the biometric module 718 can use the electrical potential sensor 223 to track the electrodermal activity of the human user 308 for detecting a stress level. In this example, the human user 308 can witness a traumatic event such as a car accident or criminal act and the biometric module 718 can detect a surge in the electrodermal activity of the human user 308 exceeding the biometric marker 530.

Moreover, the identification module 726 can identify a smartphone representing the further device 602 carried by the human user 308. In this case, the connection module 730 can generate the connection setting 608 by enabling the first communication unit 216 of the attachable device 302 to communicate with the further device 602. In addition, the connection module 730 can signal the further device 602 to capture a digital image of the traumatic event causing the rise in the electrodermal activity of the human user 308.

The multi-device module 724 can be part of the first software 226, the second software 242, or a combination thereof. The first control unit 212 can execute the first software 226, the second control unit 234 can execute the second software 242, or a combination thereof to identify the further device 602 and generate the connection setting 608 for communicating with the further device 602. Moreover, the multi-device module 724 can also communicate the connection setting 608 between devices through the first communication unit 216, the second communication unit 236, or a combination thereof.

Figure 8:
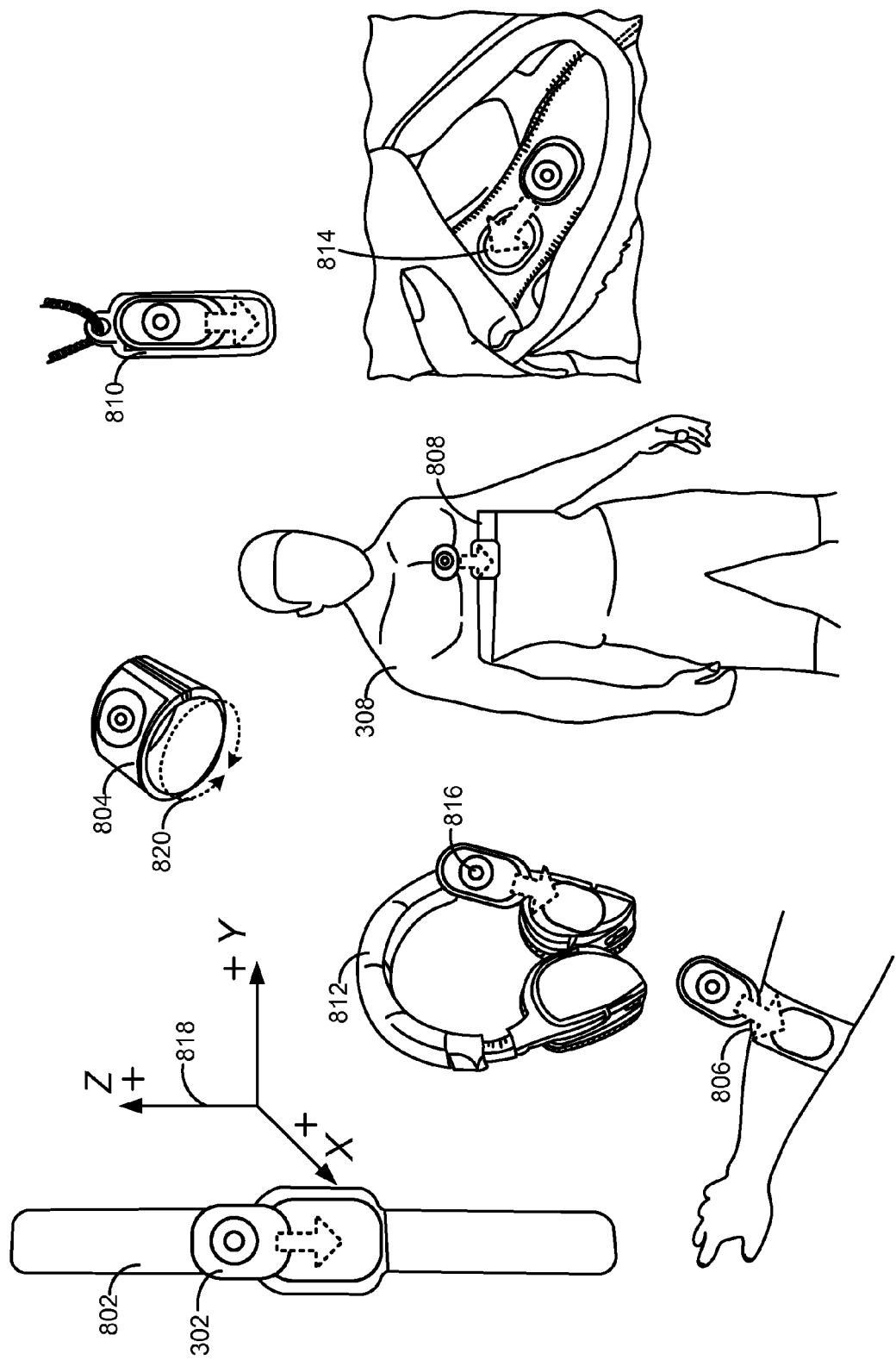
FIG. 8 is an example diagram of another embodiment of the electronic system.

Referring now to FIG. 8, therein is shown another embodiment of the electronic system 100 of FIG. 1 with the attachable device 302 configured to be attached to or housed in a holding device 802. The holding device 802 is an instance of the fastening unit 103 of FIG. 3 configured to attach or secure the attachable device 302 to the carrier 304 of FIG. 3. The holding device 802 can include a wristband holder 804, an armband holder 806, a chest strap holder 808, a pendant holder 810, a headset holder 812, a footwear holder 814, or a combination thereof.

The location module 710 of FIG. 7 can determine the attachment location 314 of FIG. 3 of the attachable device 302 based on an identity of the holding device 802. As a more specific example, each instance of the holding device 802 can be associated with a corresponding instance of the attachment location 314. For example, the electronic system 100 of FIG. 1 can associate the wristband holder 804 with a wrist region of the carrier 304. As an additional example, the electronic system 100 can associate the chest strap holder 808 with a chest region of the carrier 304.

The location module 710 can determine the attachment location 314 by determining the identity of holding device 802. The location module 710 can determine the identity of the holding device 802 by reading a communication tag 816 of the holding device 802.

The communication tag 816 is a chip, circuit, or hardware component configured to transmit identification information wirelessly. For example, the communication tag 816 can include a radio-frequency identification (RFID) tag, an NFC tag, or a combination thereof. Each instance of the holding device 802 can have its own unique instance of the communication tag 816. The location module 710 can determine the attachment location 314 when the attachable device 302 reads the communication tag 816 of the holder 804 containing identification information.

The location module 710 can also determine the attachment location 314 based on an insertion orientation 818 of the attachable device 302 into the holding device 802. The insertion orientation 818 is a geospatial orientation of a device for attaching to or inserting into another device. For example, the insertion orientation 818 can be the geospatial orientation of the attachable device 302 for attaching to or inserting into the holding device 802. Each instance of the holding device 802 can require the attachable device 302 to adopt a unique instance of the insertion orientation 818.

For example, the attachable device 302 can have a default orientation of x-axis=0°, y-axis=0°, and z-axis=0°. In this example, the wristband holder 804 can require the attachable device 302 to adopt the insertion orientation 818 of x-axis=90°, y-axis=0°, and z-axis=90° to be properly inserted into the wristband holder 804. The location module 710 can use the multi-axis gyroscope of the inertial measurement unit 221 of FIG. 2 to determine the insertion orientation 818 of the attachable device 302. The location module 710 can then determine the attachment location 314 by associating the insertion orientation 818 of the attachable device 302 with the holding device 802.

The location module 710 can also determine the attachment location 314 based on a circumference change 820 of an elastic strap or band of the holding device 802. The circumference change 820 is a difference in the circumferential length of the elastic strap or band of the holding device 802 from a default length. The circumference change 820 can occur when the holding device 802 is placed around a limb or body part of the carrier 304.

The electronic system 100 can associate different instances of the circumference change 820 with different instances of the attachment location 314. For example, the electronic system 100 can associate the attachment location 314 of a wrist of the carrier 304 with the circumference change 820 of +1.0 cm. As an additional example, the electronic system 100 can associate the attachment location 314 of a thigh of the carrier 304 with the circumference change 820 of +10.0 cm.

The electronic system 100 can estimate the circumference change 820 based on strain sensors embedded in the elastic strap or band of the holding device 802. Alternatively, electronic system 100 can approximate the circumference change 820 based on a measurement of the radial force exerted on the elastic strap or band of the holding device 802. For example, force sensors can be embedded in the elastic strap or band of the holding device 802.

In one example usage scenario, the human user 308 can insert the attachable device 302 in the wristband holder 804 in the morning when the human user 308 goes out for her morning jog. The location module 710 can automatically determine the attachment location 314 as a wrist of the human user 308 by reading the communication tag 816 of the wristband holder 804.

The inference module 714 of FIG. 7 can then determine the inferred usage 516 of FIG. 5 of the attachable device 302 as the activity tracker 524 of FIG. 5. The energy module 716 of FIG. 7 can then generate the energy saving setting 510 of FIG. 5 by enabling the gyroscope and accelerometer components of the location unit 220 of FIG. 2 and disabling the first display interface 230 of FIG. 2, the electrical potential sensor 223 of FIG. 2, the audio unit 227 of FIG. 2, the response unit 225 of FIG. 2, or a combination thereof.

Later in the morning, the human user 308 can remove the attachable device 302 from the wristband holder 804 and place the attachable device 302 in the armband holder 806 when the human user 308 has returned from her morning jog. The location module 710 can determine the attachment location 314 as the forearm of the human user 308 based on the insertion orientation 818 of the attachable device 302 into the armband holder 806.

In addition, the context module 702 of FIG. 7 can determine the usage context 508 of FIG. 5 as the indoor environment and the motion module 704 of FIG. 7 can detect the activity 502 of FIG. 5 as exhibiting little geographic movement. The inference module 714 can then determine the inferred usage 516 of the attachable device 302 as the electromyography detector 526 of FIG. 5 to control a household appliance, such as a television or computing system, in the vicinity of the attachable device 302.

Based on these determinations, the energy module 716 can generate the energy saving setting 510 by enabling the electrical potential sensor 223 and the first communication unit 216. In addition, the energy module 716 can disable the gyroscope and accelerometer components of the location unit 220, the first display interface 230, the audio unit 227, the response unit 225, or a combination thereof.

At midday, the human user 308 can remove the attachable device 302 from the armband holder 806 and insert the attachable device 302 into the headset holder 812. The location module 710 can determine the attachment location 314 as near an ear of the human user 308 by reading the communication tag 816 of the headset holder 812.

The inference module 714 can then determine the inferred usage 516 of the attachable device 302 as the headset 520 of FIG. 5. The energy module 716 can then generate the energy saving setting 510 of FIG. 5 by enabling the audio unit 227 and the Bluetooth™ component of the first communication unit 216 and disabling the electrical potential sensor 223.

In the afternoon, the human user 308 can remove the attachable device 302 from the headset holder 812 and insert the attachable device 302 into the chest strap holder 808. The location module 710 can determine the attachment location 314 as a chest region of the human user 308 based on the insertion orientation 818 of the attachable device 302 into the chest strap holder 808. The inference module 714 can then determine the inferred usage 516 of the attachable device 302 as the heart rate monitor 522 of FIG. 5.

The energy module 716 can then generate the energy saving setting 510 by enabling the electrical potential sensor 223 to monitor ECG signals and a microphone component of the audio unit 227 to listen for respiratory abnormalities. In addition, the energy module 716 can also enable the gyroscope and accelerometer components of the inertial measurement unit 221 to measure chest vibrations.

Later in the afternoon, the human user 308 can remove the attachable device 302 from the chest strap holder 808 and insert the attachable device 302 into the pendant holder 810 to use the attachable device 302 as a fashion accessory. The location motion 710 can identify the pendant holder 810 by reading the communication tag 816 of the pendant holder 810. The energy module 716 can generate the energy saving setting 510 by disabling the inertial measurement unit 221 and the electrical potential sensor 223. In addition, the energy module 716 can enable the first display interface 230 to display a color matching an outfit of the human user 308.

At nighttime, the human user 308 can remove the attachable device 302 from the pendant holder 810 and insert the attachable device 302 into the footwear holder 814. The location module 710 can determine the attachment location 314 as near the foot of the human user 308 based on the insertion orientation 818 of the attachable device 302 into the footwear holder 814. The energy module 716 can generate the energy saving setting 510 by disabling the first display interface 230 and enabling the inertial measurement unit 221 to track the activity level of the human user 308.

In another example usage scenario, the human user 308 can use multiple instances of the attachable device 302 and the holding device 802 to collaborate with a virtual reality headset. In this example, the identification module 726 of FIG. 7 can identify the virtual reality headset as the further device 602 of FIG. 6. In addition, the human user 308 can wear multiple instances of the holding device 802 including the armband holder 806 on a forearm, the chest strap holder 808 near a chest region, the headset holder 812 near an ear, and the footwear holder 814 near a foot. The human user 308 can then insert an instance of the attachable device 302 into each instance of the holding device 802.

The collaboration module 728 can determine the collaboration context 604 of FIG. 6 as a gaming environment based on the collaboration arrangement 606 of FIG. 6. The connection module 730 can then generate the connection setting 608 of FIG. 6 by working with the energy module 716 to enable or disable certain hardware components or software components of the attachable device 302.

For example, the energy module 716 can enable the electrical potential sensor 223 and the first communication unit 216 of the attachable device 302 in the armband holder 806 so the human user 308 can use the attachable device 302 in the armband holder 806 as a game controller. In this example, the attachable device 302 in the armband holder 806 can be used to interact with objects and characters in the virtual world generated by the virtual reality headset. In addition, the energy module 716 can generate the energy saving setting 510 by disabling the inertial measurement unit 221, the first display interface 230, the audio unit 227, the response unit 225, or a combination thereof of the attachable device 302 in the armband holder 806.

The energy module 716 can also enable the electrical potential sensor 223 of the attachable device 302 in the chest strap holder 808 to measure the ECG signal of the human user 308 during game play. The electronic system 100 can communicate the ECG signal of the human user 308 to the virtual reality headset to adjust the gaming environment to keep the biometric indicator 514 of FIG. 5 of the human user 308 within a threshold range.

Moreover, the energy module 716 can enable the audio unit 227 of the attachable device 302 in the headset holder 812 to enable the human user 308 to communicate audibly with other players or characters in the gaming environment. In addition, the energy module 716 can enable the gyroscope and accelerometer components of the inertia measurement unit 221 of the attachable device 302 in the footwear holder 814 so a foot of the human user 308 can be used as a game controller.

Figure 9:
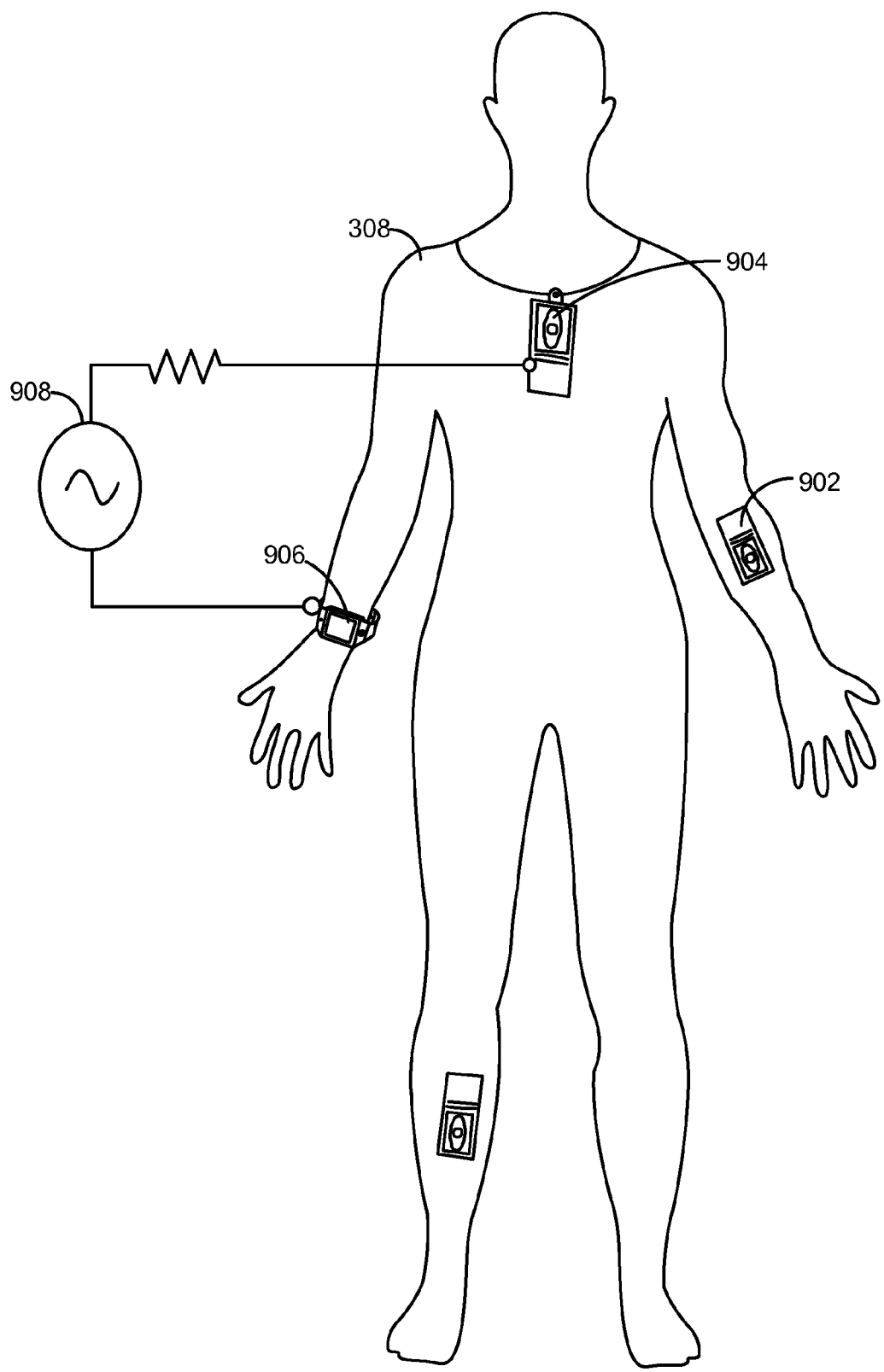
FIG. 9 is an example diagram of yet another embodiment of the electronic system.

Referring now to FIG. 9, therein is shown yet another embodiment of the electronic system 100 of FIG. 1 with the attachable device 302 of FIG. 3 implemented as a patch holder 902. The patch holder 902 is configured to accommodate and interact with a sensor patch 904. The sensor patch 904 is a wearable device or adhesive for conducting health monitoring, diagnostic testing, identification authentication, or a combination thereof on a wearer.

The sensor patch 904 can include chemical sensors or molecular sensors. For example, the sensor patch 904 can include a temperature sensor, a blood pressure sensor, a blood glucose sensor, a bio-signal sensor, a drug delivery sensor, an identification sensor, an athletic monitoring sensor such as an electrolyte sensor, a hydration sensor, a sweat sensor, a lactic acid, or a combination thereof. The sensor patch 904 can also be a one-time use sensor or a disposable sensor.

The patch holder 902, the sensor patch 904, or a combination thereof can be affixed or attached to the carrier 304 of FIG. 3 including the human user 308 through a polymeric adhesive, a collagen-based adhesive such as isinglass, an acrylate adhesive, a hydrocolloid adhesive, or a combination thereof. In some instances, the patch holder 902 and the sensor patch 904 can be affixed or attached to the human user 308 more tightly than the holding device 802 of FIG. 8, thereby providing more fidelity in sensor data.

In addition to the patch holder 902 and the sensor patch 904, the electronic system 100 can also include a reference device 906. The reference device 906 is an electronic device for generating an alternating electric charge and providing a reference electrode. For example, the reference device 906 can include a wearable device such as a watch, an activity tracker, a headset, an eyewear device, a pendant, a fashion accessory, a heart rate monitor, a virtual reality device, or a combination thereof. As an additional example, the reference device 906 can include a mobile phone, a tablet device, a laptop, or a combination thereof. As yet another example, the reference device 906 can include another instance of the attachable device 302.

The location module 710 of FIG. 7 can determine the attachment location 314 of FIG. 3 of the patch holder 902 based on an impedance measurement 908. The impedance measurement 908 is a sampled voltage detected at a receiving electrode based on an alternating current generated by a reference electrode. For example, the impedance measurement 908 can be a sampled voltage detected at the patch holder 902 based on an alternating current generated by the reference device 906. As a more specific example, the impedance measurement 908 can be a sampled voltage detected at the patch holder 902 based on an alternating current generated by a watch worn by the human user 308.

In the examples above, the impedance measurement 908 can change based on the attachment location 314 of the patch holder 902. Such changes in the impedance measurement 908 is caused by the human body's natural resistance to the flow of electric charge depending on the amount of body mass the flow of electric charge travels through.

The location module 710 can determine the attachment location 314 of the patch holder 902 by comparing the impedance measurement 908 detected at the patch holder 902 with stored impedance values corresponding to locations on a human body. The stored impedance values can be predetermined by the electronic system 100 or retrieved from a database. The stored impedance values can also be adjusted by the electronic system 100 based on input from the human user 308.

The sensor patch 904 can include an identification sticker. The identification sticker is an adhesive component affecting the resistivity or impedance of the patch holder 902 when the sensor patch 904 is attached to the patch holder 902. For example, the electronic system 100 can associate each instance of the sensor patch 904 with its own unique instance of the identification sticker. The patch holder 902 can determine an identity or functionality of the sensor patch 904 based on the identification sticker affixed to the sensor patch 904.

In one example usage scenario, the human user 308 can insert an instance of the sensor patch 904 representing the athletic monitoring sensor into the patch holder 902 when the human user 308 goes out for his morning run. This particular instance of the sensor patch 904 can include chemical sensors configured to measure levels of hydration, lactic acid buildup, electrolytes, or a combination thereof of the human user 308.

The human user 308 can attach or affix the patch holder 902 to his chest region. The location module 710 can automatically determine the attachment location 314 as the chest region of the human user 308 based on the impedance measurement 908 detected at the patch holder 902. The inference module 714 of FIG. 7 can then determine the inferred usage 516 of FIG. 5 of the patch holder 902 as the heart rate monitor 522 of FIG. 5 based on the attachment location 314, the usage context 508 of FIG. 5, the identity of the sensor patch 904, or a combination thereof.

The energy module 716 of FIG. 7 can then enable various hardware and software components of the patch holder 902 including the electrical potential sensor 223 of FIG. 2, the audio unit 227 of FIG. 2, the gyroscope and accelerometer components of the inertial measurement unit 221 of FIG. 2, or a combination thereof based on the inferred usage 516. The energy module 716 can also generate the energy saving setting 510 of FIG. 5 by disabling the first display interface 230. The patch holder 902 can use the electrical potential sensor 223 to measure an electrical bio-potential signal of the human user 308 such as an ECG signal. In addition, the patch holder 902 can use the audio unit 227 to listen for respiratory abnormalities.

After his run, the human user 308 can remove the sensor patch 904 representing the athletic monitoring sensor from the patch holder 902 and insert a new instance of the sensor patch 904 representing the identification sensor. The human user 308 can then attach or affix the patch holder 902 to his wrist. The identification sensor can include an NFC chip or circuit which can be read by an NFC reader. The identification sensor can allow the human user 308 to be identified or authenticated by the NFC reader at his workplace.

The location module 710 can automatically determine the attachment location 314 as the wrist of the human user 308 based on the impedance measurement 908 detected at the patch holder 902. The patch holder 902 can also identify the identity of the sensor patch 904 as the identification sensor based on the identification sticker. The inference module 7014 can then determine the inferred usage 516 of the patch holder 902 as an identification badge based on the attachment location 314, the identity of the sensor patch 904, the usage context 508 such as the time-of-day and the day-of-the week, or a combination thereof.

In another example usage scenario, the human user 308 can insert an instance of the sensor patch 904 representing the blood glucose sensor into the patch holder 902. The human user 308 can initially attach or affix the patch holder 902 to an abdominal region. The location module 710 can automatically determine the attachment location 314 as the abdominal region of the human user 308 based on the impedance measurement 908 detected at the patch holder 902. The inference module 714 can determine the inferred usage 516 of the patch holder 902 as a glucose monitor based on the attachment location 314, the identity of the sensor patch 904, or a combination thereof.

The guidance module 722 of FIG. 7 can then generate the positioning feedback 336 of FIG. 3 to improve a diagnostic functionality of the sensor patch 904. For example, the guidance module 722 can generate the positioning feedback 335 to guide the human user 308 to move the patch holder 902 to a different region of the abdomen more suitable for blood glucose measurements.

As a more specific example, the guidance module 722 can generate the positioning feedback 336 by generating the haptic feedback 330 of FIG. 3, the audio feedback 332 of FIG. 3, the visual feedback 334 of FIG. 3, or a combination thereof. The guidance module 722 can generate the positioning feedback 336 through the response unit 225 of the patch holder 902.

As an even more specific example, the guidance module 722 can generate the visual feedback 334 as different colored lights using the first display interface 230. In this example, the guidance module 722 can generate the visual feedback 334 as a red light to indicate a non-optimal instance of the attachment location 314 for measuring blood glucose. Moreover, the guidance module 722 can generate the visual feedback 334 as a green light to indicate an instance of the attachment location 314 most suitable for measuring the blood glucose of the human user 308.

Figure 10:
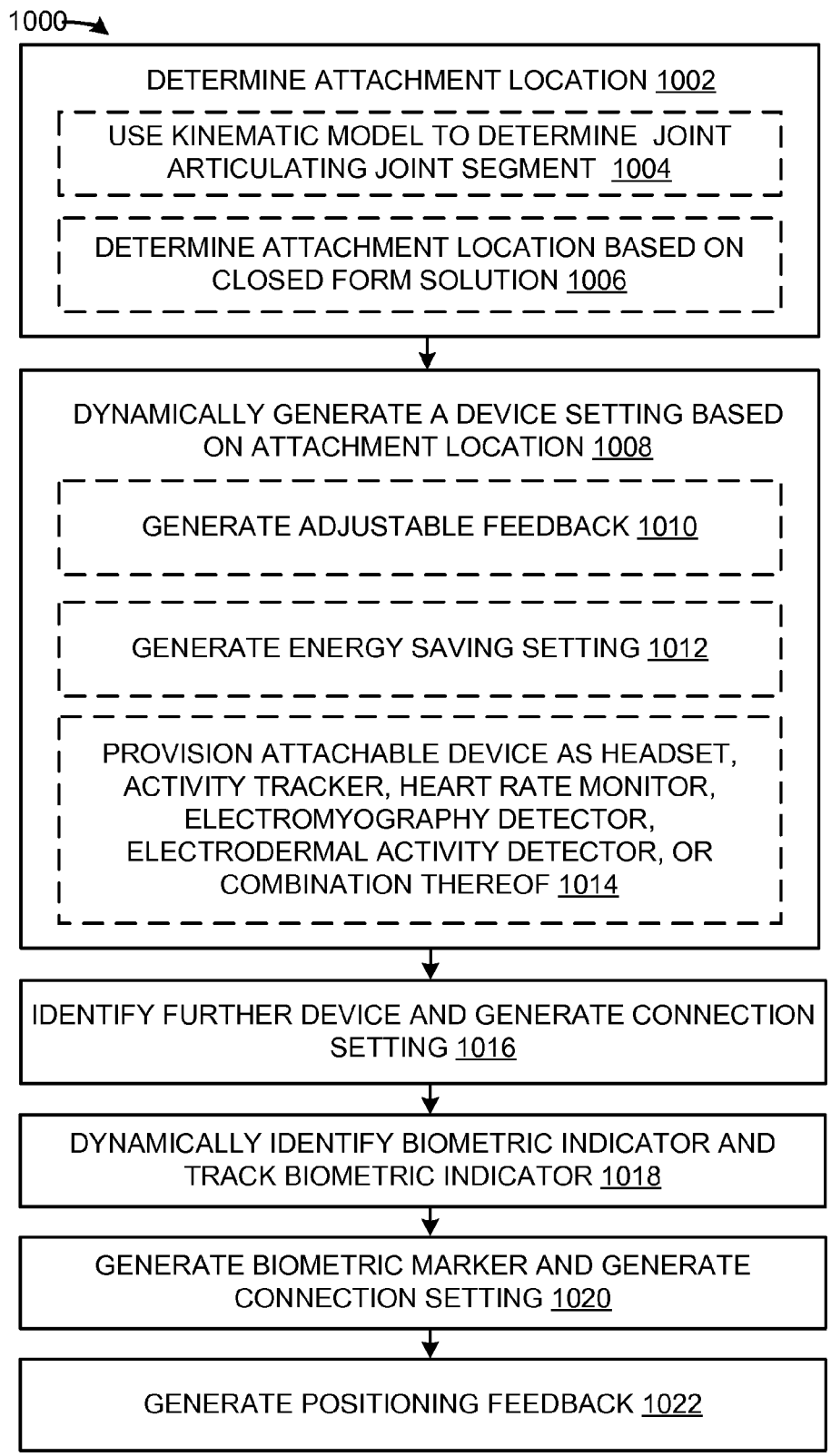
FIG. 10 is a flow chart of a method of operation of the electronic system in a further embodiment of the present invention.

Referring now to FIG. 10, therein is shown an exemplary flow chart 1000 of a method of operation of the electronic system 100 of FIG. 1 in a further embodiment. In one example embodiment, the electronic system 100 can implement the control flow 700 of FIG. 7.

The exemplary flow chart 1000 can include determining the attachment location 314 of FIG. 3 of the attachable device 302 of FIG. 3 based on the kinematic model 324 of FIG. 3 for representing the motion 320 of FIG. 3 of the carrier 304 of FIG. 3 in a box 1002. The electronic system 100 can use the location module 710 of FIG. 7 to determine the attachment location 314.

The exemplary flow chart 1000 can also include determining the attachment location 314 by using the kinematic model 324 to determine the joint 316 of FIG. 3 articulating the joint segment 318 of FIG. 3 in a box 1004. The electronic system 100 can use the modeling module 708 of FIG. 7 to access the kinematic model 324.

In addition, the exemplary flow chart 1000 can include determining the attachment location 314 based on the closed form solution 420 of FIG. 4 in a box 1006. The electronic system 100 can use the location module 710 to determine the attachment location 314 based on the closed form solution 420.

The exemplary flow chart 1000 can include generating the device setting 504 of FIG. 5 based on the attachment location 314 for provisioning the attachable device 302 in a box 1008. The electronic system 100 can use the setting module 712 of FIG. 7 to generate the device setting 504.

The exemplary flow chart 1000 can include generating the device setting 504 by generating the adjustable feedback 328 of FIG. 3 at the attachable device 302 based on the attachment location 314 in a box 1010. The electronic system 100 can use the feedback module 720 of FIG. 7 to generate the adjustable feedback 328.

The exemplary flow chart 1000 can also include generating the device setting 504 by generating the energy saving setting 510 of FIG. 5 based on the attachment location 314 in a box 1012. The electronic system 100 can use the energy module 716 of FIG. 7 to generate the energy saving setting 510.

The exemplary flow chart 1000 can also include generating the device setting 504 by provisioning the attachable device 302 as the headset 520 of FIG. 5, the activity tracker 524 of FIG. 5, the heart rate monitor 522 of FIG. 5, the electromyography detector 526 of FIG. 5, the electrodermal activity detector 528 of FIG. 5, or a combination thereof in a box 1014. The electronic system 100 can use the inference module 714 of FIG. 7 and the energy module 716 to provision the attachable device 302.

The exemplary flow chart 1000 can further include identifying the further device 602 of FIG. 6 for interacting with the attachable device 302 and generating the connection setting 608 of FIG. 6 for communicating with the further device 602 based on the collaboration context 604 of FIG. 6 and the attachment location 314 in a box 1016. The electronic system 100 can use the collaboration module 728 of FIG. 7 to identify the further device 602 and generate the connection setting 608.

The exemplary flow chart 1000 can further include identifying the biometric indicator 514 of FIG. 5 based on the attachment location 314 and tracking the biometric indicator 514 at the attachable device 302 in a box 1018. The electronic system 100 can use the biometric module 718 of FIG. 7 to identify the biometric indicator 514.

The exemplary flow chart 1000 can further include generating the biometric marker 530 of FIG. 5 based on the attachment location 314 and generating the connection setting 608 of FIG. 6 for communicating with the further device 602 based on the collaboration context 604, the biometric marker 530, or a combination thereof in a box 1020. The electronic system 100 can use the biometric module 718 to generate the biometric marker 530 and the collaboration module 728 to generate the connection setting 608.

The exemplary flow chart 1000 can further include generating the positioning feedback 336 of FIG. 3 for guiding the carrier 304 or the user of the electronic system 100 to move the attachable device 302 to a new instance of the attachment location 314 in a box 822. The electronic system 100 can use the feedback module 720 to generate the positioning feedback 336.

The modules described herein can be hardware implementation or hardware accelerators, including passive circuitry, active circuitry, or both, in the first control unit 212 of FIG. 2, the second control unit 234 of FIG. 2, or a combination thereof. The modules can also be hardware implementation or hardware accelerators, including passive circuitry, active circuitry, or both, within the first device 102, the second device 106, or a combination thereof but outside of the first control unit 212, the second control unit 234, or a combination thereof.

For illustrative purposes, the various modules have been described as being specific to the first device 102, the second device 106, or a combination thereof. However, it is understood that the modules can be distributed differently. For example, the various modules can be implemented in a different device, or the functionalities of the modules can be distributed across multiple devices. Also as an example, the various modules can be stored in a non-transitory memory medium.

As a more specific example, one or more modules described above can be stored in the non-transitory memory medium for distribution to a different system, a different device, a different user, or a combination thereof. Also as a more specific example, the modules described above can be implemented or stored using a single hardware unit, such as a chip or a processor, or across multiple hardware units.

The modules described in this application can be stored in the non-transitory computer readable medium. The first storage unit 214 of FIG. 2, the second storage unit 246 of FIG. 2, or a combination thereof can represent the non-transitory computer readable medium. The first storage unit 214, the second storage unit 246, or a combination thereof, or a portion therein can be removable from the first device 102, the second device 106, or a combination thereof. Examples of the non-transitory computer readable medium can be a non-volatile memory card or stick, an external hard disk drive, a tape cassette, or an optical disk.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of the embodiment of the present invention is that it valuably supports and services the historical trend of reducing costs, simplifying systems, and increasing performance. These and other valuable aspects of the embodiment of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. An electronic system comprising:
   a storage interface configured to:
      access a kinematic model for representing one or more motions of a carrier;
   a control unit, coupled to the storage interface, configured to:
      determine an attachment location of an attachable device based on the kinematic model; and
      generate a device setting based on the attachment location for provisioning the attachable device.

2. The system as claimed in claim 1 wherein the control unit is configured to generate the device setting by generating an adjustable feedback at the attachable device based on the attachment location.

3. The system as claimed in claim 1 wherein the control unit is further configured to:
   identify a further device for interacting with the attachable device; and
   generate a connection setting for communicating with the further device based on a collaboration context and the attachment location.

4. The system as claimed in claim 1 wherein the control unit is configured to generate the device setting by generating an energy saving setting based on the attachment location.

5. The system as claimed in claim 1 wherein the control unit is further configured to:
   identify a biometric indicator based on the attachment location; and
   track the biometric indicator at the attachable device.

6. The system as claimed in claim 1 wherein the control unit is configured to determine the attachment location by using the kinematic model to determine a joint articulating a joint segment.

7. The system as claimed in claim 1 wherein the control unit is further configured to:
   generate a biometric marker based on the attachment location; and
   generate a connection setting for communicating with a further device based on the collaboration context, the biometric marker, or a combination thereof.

8. The system as claimed in claim 1 wherein the control unit is further configured to generate a positioning feedback for attaching the attachable device to a new instance of the attachment location.

9. The system as claimed in claim 1 wherein the control unit is configured to generate the device setting by provisioning the attachable device as a headset, an activity tracker, a heart rate monitor, an electromyography detector, an electrodermal activity detector, or a combination thereof.

10. The system as claimed in claim 1 wherein the control unit is configured to determine the attachment location based on a closed form solution.

11. The system as claimed in claim 1 wherein the kinematic model includes a quantitative representation of the one or more motions of the carrier.

12. The system as claimed in claim 1 wherein the attachable device is a patch holder configured to accommodate a sensor patch.

13. A method of operation of an electronic system comprising:
   determining, with a control unit, an attachment location of an attachable device based on a kinematic model for representing one or more motions of a carrier; and
   generating a device setting based on the attachment location for provisioning the attachable device.

14. The method as claimed in claim 13 wherein generating the device setting includes generating an adjustable feedback at the attachable device based on the attachment location.

15. The method as claimed in claim 13 further comprising:
   identifying a further device for interacting with the attachable device; and
   generating a connection setting for communicating with the further device based on a collaboration context and the attachment location.

16. The method as claimed in claim 13 wherein generating the device setting includes generating an energy saving setting based on the attachment location.

17. The method as claimed in claim 13 further comprising:
   identifying a biometric indicator based on the attachment location; and
   tracking the biometric indicator at the attachable device.

18. The method as claimed in claim 13 wherein determining the attachment location includes using the kinematic model to determine a joint articulating a joint segment.

19. The method as claimed in claim 13 further comprising:
   generating a biometric marker based on the attachment location; and
   generating a connection setting for communicating with a further device based on the collaboration context, the biometric marker, or a combination thereof.

20. The method as claimed in claim 13 further comprising generating a positioning feedback for attaching the attachable device to a new instance of the attachment location.

21. The method as claimed in claim 13 wherein generating the device setting includes provisioning the attachable device as a headset, an activity tracker, a heart rate monitor, an electromyography detector, an electrodermal activity detector, or a combination thereof.

22. The method as claimed in claim 13, wherein determining the attachment location includes determining the attachment location based on a closed form solution.

23. The method as claimed in claim 13 wherein the kinematic model includes a quantitative representation of the one or more motions of the carrier.

24. The method as claimed in claim 13 wherein the attachable device is a patch holder configured to accommodate a sensor patch.

25. A non-transitory computer readable medium including instructions for execution by a control unit comprising:
   determining an attachment location of an attachable device based on a kinematic model for representing one or more motions of a carrier; and
   generating a device setting based on the attachment location for provisioning the attachable device.

26. The non-transitory computer readable medium as claimed in claim 25 wherein generating the device setting includes generating an adjustable feedback at the attachable device based on the attachment location.

27. The non-transitory computer readable medium as claimed in claim 25 further comprising:
   identifying a further device for interacting with the attachable device; and
   generating a connection setting for communicating with the further device based on a collaboration context and the attachment location.

28. The non-transitory computer readable medium as claimed in claim 25 wherein generating the device setting includes generating an energy saving setting based on the attachment location.

29. The non-transitory computer readable medium as claimed in claim 25 further comprising:
   identifying a biometric indicator based on the attachment location; and
   tracking the biometric indicator at the attachable device.

30. The non-transitory computer readable medium as claimed in claim 25 wherein determining the attachment location includes using the kinematic model to determine a joint articulating a joint segment.

31. The non-transitory computer readable medium as claimed in claim 25 further comprising:
   generating a biometric marker based on the attachment location; and
   generating a connection setting for communicating with a further device based on the collaboration context, the biometric marker, or a combination thereof.

32. The non-transitory computer readable medium as claimed in claim 25 further comprising generating a positioning feedback for attaching the attachable device to a new instance of the attachment location.

33. The non-transitory computer readable medium as claimed in claim 25 wherein generating the device setting includes provisioning the attachable device as a headset, an activity tracker, a heart rate monitor, an electromyography detector, an electrodermal activity detector, or a combination thereof.

34. The non-transitory computer readable medium as claimed in claim 25 wherein determining the attachment location includes determining the attachment location based on a closed form solution.

35. The non-transitory computer readable medium as claimed in claim 25 wherein the kinematic model includes a quantitative representation of the one or more motions of the carrier.

36. The non-transitory computer readable medium as claimed in claim 25 wherein the attachable device is a patch holder configured to accommodate a sensor patch.

* * * * *